United States Patent
Sloan et al.

(10) Patent No.: US 10,012,540 B2
(45) Date of Patent: *Jul. 3, 2018

(54) FABRY-PEROT INTERFEROMETER BASED SATELLITE DETECTION OF ATMOSPHERIC TRACE GASES

(71) Applicant: GHGSat Inc., Montreal (CA)

(72) Inventors: James J. Sloan, Wettingen (CH); Berké Durak, Montreal (CA); David Gains, Kanata (CA); Francesco Ricci, Ville Mont-Royal (CA); Jason McKeever, Montreal (CA); Joshua Lamorie, Longueuil (CA); Mark Sdao, Montreal (CA); Vincent Latendresse, Montreal (CA); Jonathan Lavoie, Montreal (CA); Roman Kruzelecky, Beaconsfield (CA)

(73) Assignee: GHGSAT INC., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/314,001

(22) PCT Filed: May 1, 2015

(86) PCT No.: PCT/CA2015/050374
§ 371 (c)(1),
(2) Date: Nov. 25, 2016

(87) PCT Pub. No.: WO2015/179965
PCT Pub. Date: Dec. 3, 2015

(65) Prior Publication Data
US 2017/0191873 A1    Jul. 6, 2017

Related U.S. Application Data

(60) Provisional application No. 62/003,289, filed on May 27, 2014.

(51) Int. Cl.
*G01J 3/26* (2006.01)
*G01J 3/28* (2006.01)
(Continued)

(52) U.S. Cl.
CPC . *G01J 3/26* (2013.01); *G01J 3/28* (2013.01); *G01J 3/2823* (2013.01); *G01J 3/42* (2013.01);
(Continued)

(58) Field of Classification Search
CPC ........ G01J 3/26; G01J 3/42; G01J 3/28; G01J 3/2823; G01N 2021/1793; G02F 2001/213; G01L 1/0079
See application file for complete search history.

(56) References Cited

U.S. PATENT DOCUMENTS

| | | | | |
|---|---|---|---|---|
| 3,984,190 A | * | 10/1976 | Barrett | G01J 3/26 356/301 |
| 4,035,643 A | * | 7/1977 | Barrett | G01J 3/26 250/339.13 |

(Continued)

FOREIGN PATENT DOCUMENTS

EP    1867969 A1    12/2007

OTHER PUBLICATIONS

John Wellman, Imaging Spectrometers for Terrestrial and Planetary Remote Sensing: A progress Reprot, Jan. 12, 1987, SPIE 0750, pp. 140-151.*

(Continued)

*Primary Examiner* — Michael P Lapage
(74) *Attorney, Agent, or Firm* — Brion Raffoul

(57) ABSTRACT

Systems, methods, and devices relating to optical imaging systems for gathering data on atmospheric trace gas emissions from a satellite. An optical system used in the satellite has a Fabry-Perot interferometer coupled to a suitable telescope. The interferometer is a wide angle Fabry-Perot inter-
(Continued)

ferometer which creates a fringing pattern in concentric circles with each fringe being a different wavelength on the imaging system. A filter is used with the optical system and allows multiple adjacent modes in a selected spectral range to pass through the interferometer to the imaging system. Each pixel in the imaging system collects light at multiple wavelengths within the selected spectral range. The optical system gathers multiple images of the target area allowing light from the target area to be collected at multiple different wavelengths. Different absorption data for different atmospheric trace gases can be gathered in a single satellite pass over the target area.

11 Claims, 20 Drawing Sheets

(51) Int. Cl.
*G01J 3/42* (2006.01)
*G02F 1/21* (2006.01)
*G01N 21/17* (2006.01)
*G01N 21/3504* (2014.01)

(52) U.S. Cl.
CPC .......... *G01N 2021/1793* (2013.01); *G01N 2021/3531* (2013.01); *G02F 2001/213* (2013.01)

(56) References Cited

U.S. PATENT DOCUMENTS

| | | | |
|---|---|---|---|
| 4,615,033 A | 9/1986 | Nakano et al. | |
| 4,765,736 A | 8/1988 | Gallagher et al. | |
| RE35,355 E | 10/1996 | Ryan et al. | |
| 5,606,419 A * | 2/1997 | Foosnæs | G01J 3/26 356/419 |
| 5,801,831 A | 9/1998 | Sargoytchev | |
| 5,835,214 A * | 11/1998 | Cabib | G06K 9/76 356/452 |
| 7,030,991 B1 | 4/2006 | Kampe | |
| 7,050,215 B1 | 5/2006 | Johnson et al. | |
| 7,561,274 B2 * | 7/2009 | Brady | G01J 3/18 356/454 |
| 7,893,408 B2 | 2/2011 | Hieftje et al. | |
| 2002/0191268 A1 | 12/2002 | Seeser et al. | |
| 2005/0046837 A1 * | 3/2005 | Izumi | G01J 3/18 356/326 |
| 2006/0119861 A1 * | 6/2006 | Saunders | G01B 11/2441 356/512 |
| 2008/0259340 A1 | 10/2008 | Prasad et al. | |
| 2013/0228688 A1 * | 9/2013 | Plusquellic | G01J 3/108 250/339.06 |

OTHER PUBLICATIONS

Wilson, Emily L., "Development of a Fabry-Perot interferometer for ultra-precise measurements of col. CO2", Measuring Science and Technology, vol. 18/5, Mar. 27, 2007, pp. 1495-1502.
ISA/CA, International Search Report and Written Opinion for PCT/CA2015/050374 dated Jul. 13, 2015.
Extended European Search Report for corresponding EP Patent Application No. 15799973.1, dated Nov. 13, 2017.
Kuhn, J. "A Fabry-Perot Interferometer-based camera for two-dimensional mapping of SO2 distributions", Atmospheric Measurement Techniques, vol. 7, No. 11, May 22, 2014, pp. 3705-3715, XP054419309.
Wallace, J. "Optical Fabrication: Fluid-jet polisher is deterministic—Laser Focus World", Laser Focus World Magazine, Mar. 1, 2017, XP055419967.
Giovannelli, L. "The birth of Tor Vergata Fabry-Perot interferometer", Journal of Physics: Conference Series, Institute of Physics Publishing, Bristol, vol. 383, No. 1, Oct. 1, 2012, p. 12014, XP020230689.

\* cited by examiner

FABRY-PEROT INTERFEROMETER BASED SATELLITE DETECTION OF ATMOSPHERIC TRACE GASES

TECHNICAL FIELD

The present invention relates to optical systems for use in satellites. More specifically, the present invention relates to optical systems for use in detecting atmospheric trace gas emissions from specific target locations by way of an observation platform overflying those target locations.

BACKGROUND OF THE INVENTION

The growing awareness of environmental issues in the last fifty years has led to a greater need for more environmentally friendly systems and devices. This growing awareness has also led to a need for better monitoring of potentially environmentally harmful atmospheric emissions from industrial facilities.

Currently, harmful atmospheric emissions can be monitored using, among others, continuous emissions monitoring systems installed at industrial facilities. As well, several large scientific satellite systems have been developed to measure atmospheric trace gases; these satellite systems include Europe's Envisat, the United States' Orbiting Carbon Observatory, and Japan's Greenhouse Gas Observing Satellite.

One drawback of current satellite solutions is that they trade-off swath size for spatial resolution. In order to obtain measurements for the whole planet, current satellites measure several hundred, or even thousands of kilometers, of swath for each orbital path. The highest spatial resolution is therefore currently in the order of single digit kilometers. This makes it difficult to identify atmospheric emissions from individual industrial facilities.

Another drawback with current satellite solutions is that they cannot collect sufficient light at desired wavelengths in each pass to enable measurement of atmospheric trace gases from individual industrial facilities. Several factors, such as the speed at which satellites pass over specific areas, the number of images taken of the specific areas in each pass, and the throughput of their optical systems, contribute to this drawback.

There is therefore a need for systems, methods, and devices which mitigate if not overcome the shortcomings of the prior art for measuring environmentally harmful atmospheric emissions from industrial facilities.

SUMMARY OF INVENTION

The present invention provides systems, methods, and devices relating to optical imaging systems for gathering data on atmospheric trace gas emissions from a satellite. An optical system for deployment in a satellite has a Fabry-Perot interferometer coupled to a suitable telescope. The image received from the telescope passes through the interferometer before being received by an imaging system. The interferometer is a wide angle Fabry-Perot interferometer. This interferometer creates a fringing pattern of concentric rings with each fringe being at a different wavelength on the imaging system. The interferometer also has a large aperture to maximize light throughput and a high finesse to provide high spectral resolution, which enable measurements at precise wavelengths at each pixel in the imaging system. A filter is used with the optical system such that multiple adjacent modes in a selected spectral range are allowed to pass through the interferometer to the imaging system. In each image, each pixel in the imaging system collects light at multiple wavelengths within the selected spectral range. In addition, during a pass of the satellite over the target area, the target area tracks across the field of view of the optical system, thereby allowing the optical system to gather multiple images of the target area. Since the position of the target area within the field of view changes for every image, light at multiple wavelengths is collected from each ground pixel in the target area. In this way, different absorption data for different atmospheric trace gases can be gathered in a single satellite pass over the target area.

In a first aspect, the present invention provides a method for detecting atmospheric trace gas emissions at a specific target location from an observation platform, the method comprising:
a) providing an image gathering device at said platform, said platform overflying said specific target location;
b) providing a wide angle Fabry-Perot interferometer at said platform such that light gathered from said specific target location passes through said interferometer before being received by said image gathering device, said interferometer allowing said atmospheric trace gas emissions for a target area to be measured using light at multiple wavelengths;
c) determining a spectral response of a plurality of pixels on said image gathering device to said light gathered from said specific target location based on a traversal angle for said interferometer;
d) recursively adjusting parameters of a predetermined model and recursively comparing said spectral response from said image gathering device with results from said model to determine vertical column densities of said atmospheric trace gases at said specific target locations, said vertical column densities being values which account for relevant atmospheric spectroscopy and a full instrument response from devices on said platform.

In a second aspect, the present invention provides a method for detecting atmospheric trace gas emissions at a specific target location, the method comprising:
a) providing an image gathering device at an observation platform, said platform being used to overfly said specific target location;
b) providing a Fabry-Perot interferometer at said platform such that light at multiple wavelengths gathered at said specific target location passes through said interferometer before being received by said image gathering device, said interferometer also having a large aperture which maximizes light throughput and a high finesse which provides high spectral resolution, said large aperture and high finesse enabling measurements at precise wavelengths at each pixel in said image gathering device;
c) applying a filter to said interferometer such that said filter allows multiple modes in a selected spectral range to pass through said filter, said multiple modes allowed through being modes adjacent to one another;
d) determining the vertical column densities of said atmospheric trace gases said specific target location using signals from said image gathering device.

In a third aspect, the present invention provides a method for detecting atmospheric trace gas emissions from a specific target location, the method comprising:
a) providing an image gathering device at an observation platform, said platform being used to overfly said specific target location;
b) providing a wide-angle, high-finesse Fabry-Perot interferometer at said satellite such that light gathered from a specific target location passes through said interferometer before being received by said image gathering device;

c) gathering multiple images for said specific target location as said platform passes above said specific target location to thereby simultaneously gather data for multiple atmospheric trace gas emissions;

d) applying a filter to said interferometer such that said filter allows multiple modes in a selected spectral range to pass through said filter, said multiple modes allowed through being modes adjacent to one another;

e) determining vertical column spectral densities of said atmospheric trace gas emissions from a spectra resulting from said light in said multiple images.

In a fourth aspect, the present invention provides a method for detecting atmospheric trace gas emissions on a planet from a satellite, the method comprising:

a) providing an image gathering device at said satellite, said satellite being in orbit about said planet;

b) providing a wide-angle, high-finesse Fabry-Perot interferometer at said satellite such that light gathered from said specific target location on said planet passes through said interferometer before being received by said image gathering device;

c) gathering multiple images for said specific target location as said satellite passes above said specific target location;

d) applying a filter to said interferometer such that said filter allows multiple modes in a selected spectral range to pass through said filter to said image gathering device;

e) determining a spectral response of a plurality of pixels on said image gathering device to said light gathered from said specific target location based on a traversal angle for said interferometer;

f) recursively adjusting parameters of a predetermined model and recursively comparing said spectral response from said image gathering device with results from said model to determine vertical column densities of said atmospheric trace gases at said specific target location, said vertical column densities being values which account for relevant atmospheric spectroscopy and a full instrument response from devices on said platform.

In a fifth aspect, the present invention provides a system for detecting atmospheric trace gas emissions from a specific target location by way of an observation platform, the system comprising:

an image gathering device located at said platform, said platform being for overflying said specific target location, said image gathering device being for gathering multiple images of said specific target location as said platform overflies said specific target location;

a wide-angle, high finesse Fabry-Perot interferometer, said interferometer being located at said platform and being configured such that light gathered from said specific target location passes through said interferometer before being received by said image gathering device; and a filter for filtering light from said specific target location prior to being received by said interferometer, said filter being for allowing multiple modes in a selected spectral range to pass through said filter to said image gathering device.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
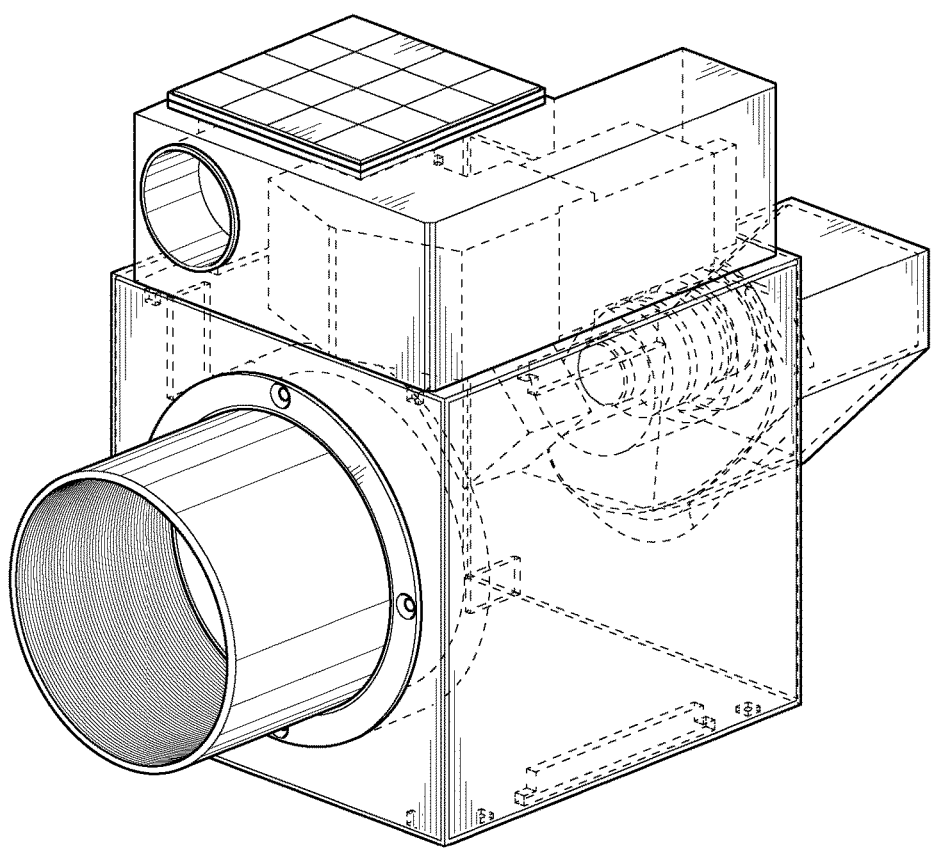
FIG. 1 illustrates one embodiment of the optical system of the invention as a satellite payload.

In one embodiment, the present invention provides systems and devices for use in satellite-based applications for gathering data on atmospheric trace gas emissions from target locations. The invention involves the use of a Fabry-Perot interferometer in the gathering of image data to determine atmospheric trace gas emissions. The interferometer is a wide angle interferometer which creates a fringing pattern on the imaging system, enabling measurement of multiple wavelengths in each image. The interferometer also has a large aperture to maximize light throughput and a high finesse to provide high spectral resolution, which enable measurements at precise wavelengths at each pixel in the imaging system. A filter is used with the optical system such that multiple adjacent modes in a selected spectral range are allowed to pass through the interferometer to the imaging system. In each image, each pixel in the imaging system therefore collects light at multiple wavelengths within the selected spectral range. In addition, during a pass of the satellite over the target area, the target area tracks across the field of view of the optical system, thereby allowing the optical system to gather multiple images of the target area. Since the position of the target area within the field of view changes for every image, light at multiple wavelengths is collected from each ground pixel in the target area. In this way, different absorption data for different atmospheric trace gases can be gathered in a single satellite pass over the target area.

It should be clear that while the examples provided below relate to a satellite mounted embodiment of the invention, other platforms are possible. The invention may be implemented on any aerial platform including but not limited to manned and unmanned aerial vehicles and all forms of satellites.

In a sixth aspect, this document discloses a system for detecting atmospheric trace gas emissions from a specific target location by way of an observation platform, the system comprising:
  an image gathering device located at said platform, said platform being for overflying said specific target location, said image gathering device being for gathering multiple images of said specific target location as said platform overflies said specific target location;
  a Fabry-Perot interferometer having a range of angles, said interferometer being located at said platform and being configured such that light gathered from said specific target location passes through said interferometer before being received by said image gathering device; and
  a filter for filtering light from said specific target location prior to being received by said interferometer, said filter being for allowing multiple modes in a selected spectral range to pass through said filter to said image gathering device;
  wherein said Fabry-Perot interferometer comprises at least two mirrors, each of said at least two mirrors having the following characteristics:
    a surface roughness of less than 1 nm rms;
    a surface curvature of less than 2 nm; and
    a surface tilt of less than 2 nm.

Figure 2A:
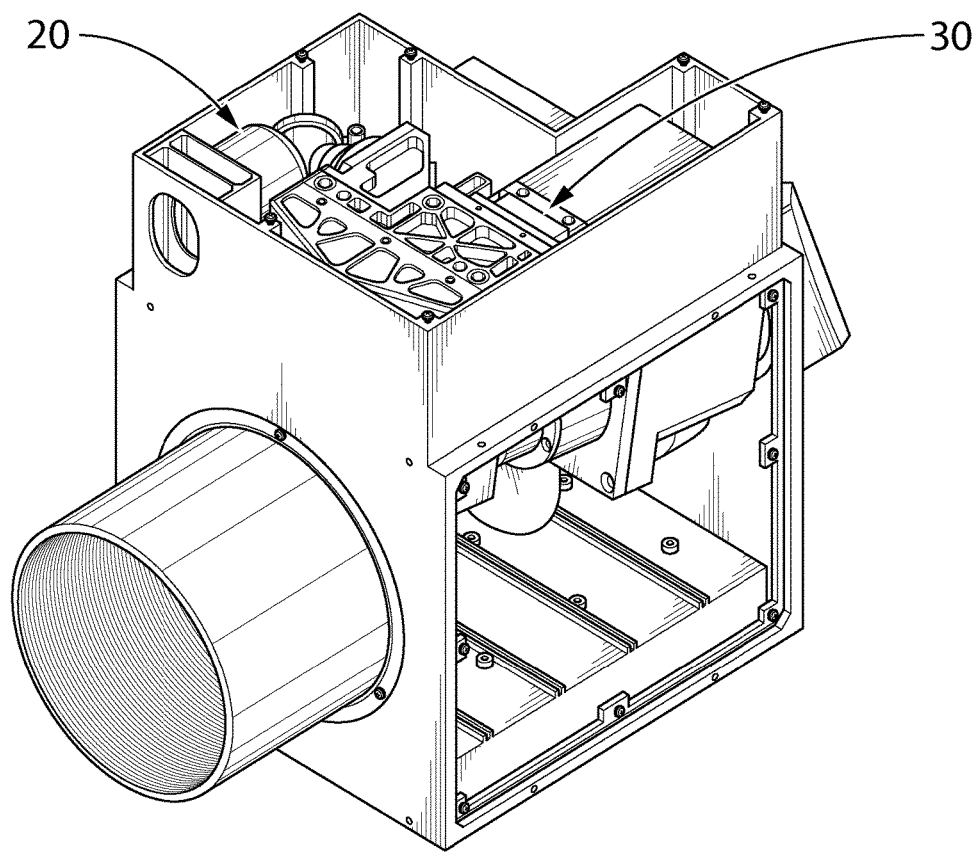
FIGS. 2A and 2B illustrate the various components of the optical system in FIG. 1.
Figure 2B:
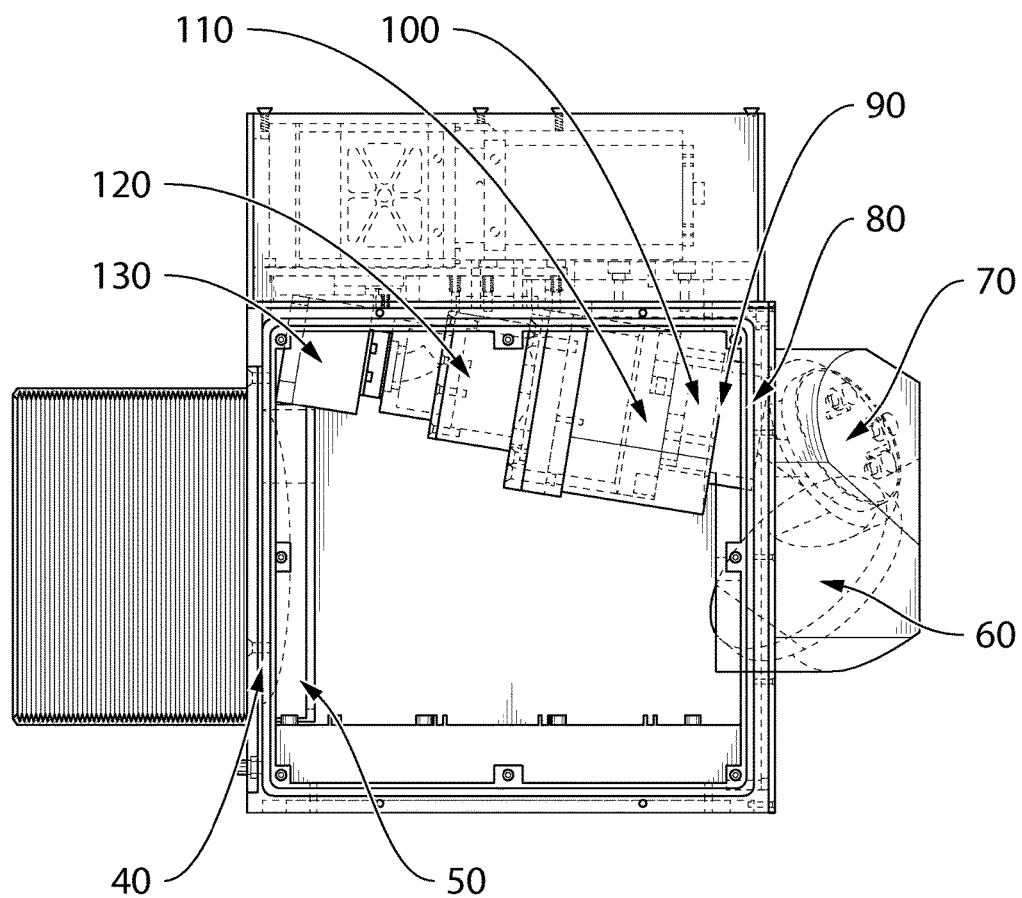

Referring to FIG. 1, an illustration of one embodiment of the optical system as a satellite payload is illustrated. Referring to FIGS. 2A and 2B, the various components of the optical system are illustrated. A cloud and aerosol telescope 20 and a cloud and aerosol spectrometer 30 are side by side with the optical system.

Referring to FIG. 2B, a baffle 40 is adjacent to a first telescopic lens 50 at one end of the optical system 10. At another end is a first beam folding mirror 60 adjacent a second beam folding mirror 70. Two collimating lenses 80 receive input from the beam folding mirror 70. The output of the collimating lenses 80 is then filtered by an order sorting filter 90 and is then received by a further collimating lens 100. From the collimating lens 100, light is then passed through a Fabry-Perot interferometer 110. Light passing through the interferometer 110 is then received by imaging lenses 120. Finally, what passes through the imaging lenses 120 is then received and recorded by an SWIR (short-wave infrared) camera 130.

In one embodiment, the satellite carrying the payload will be in sun-synchronous orbit, between an altitude of 650 and 750 km, depending on the launcher used.

Figure 3:
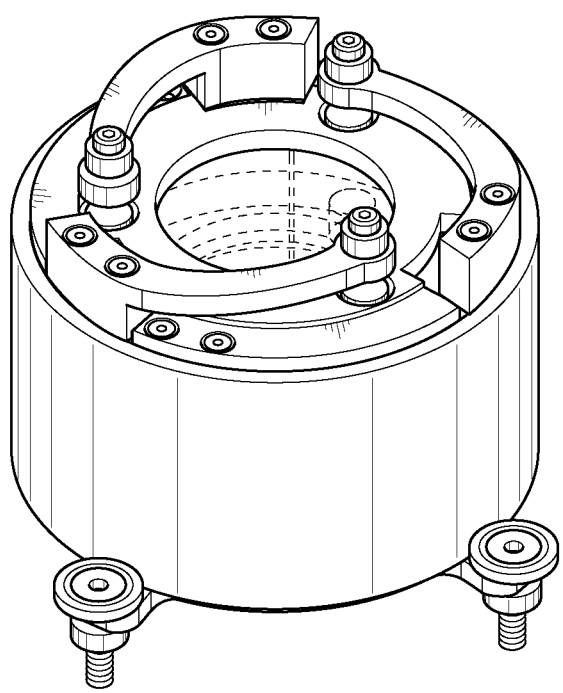
FIG. 3 is a perspective view of the Fabry-Perot interferometer assembly.
Figure 4:
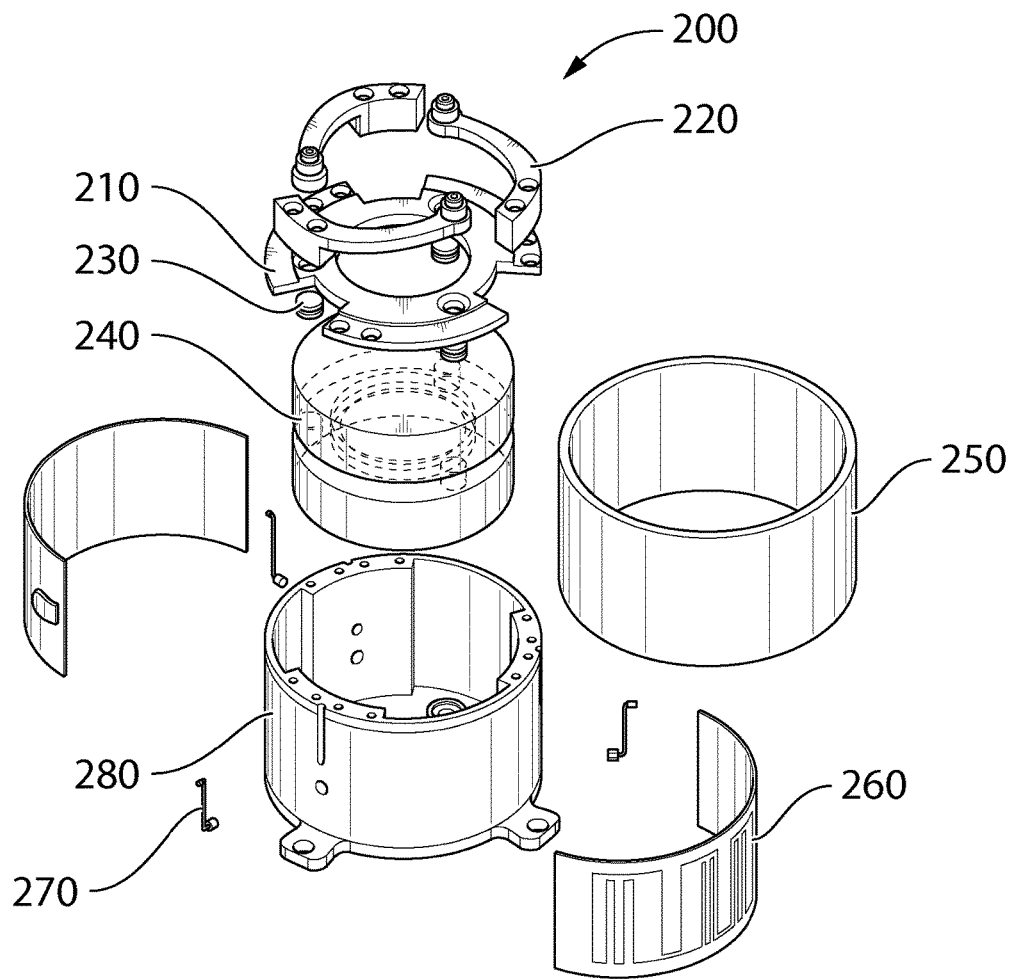
FIG. 4 is an exploded view of the interferometer assembly of FIG. 3.

Referring to FIG. 3, a perspective view of the Fabry-Perot interferometer assembly is illustrated. Referring to FIG. 4, an exploded view of the interferometer assembly 200 is illustrated. The interferometer assembly 200 has a cover 210 and a flexure 220. Pushers 230 transfer a preload from each flexure 220 to the optical component 240, to enable the interferometer to better withstand launch vibrations. A thermal blanket 250 surrounds the components for insulation while a heater 260 is provided to maintain optical component 240 at an optimal operating temperature. A temperature sensor 270 is also provided to determine the temperature of the assembly 200. The heater 260 is deployed outside a housing 280 which houses the various components of the assembly 200.

To assist in understanding the invention, an explanation of a Fabry-Perot interferometer is provided.

Figure 5:
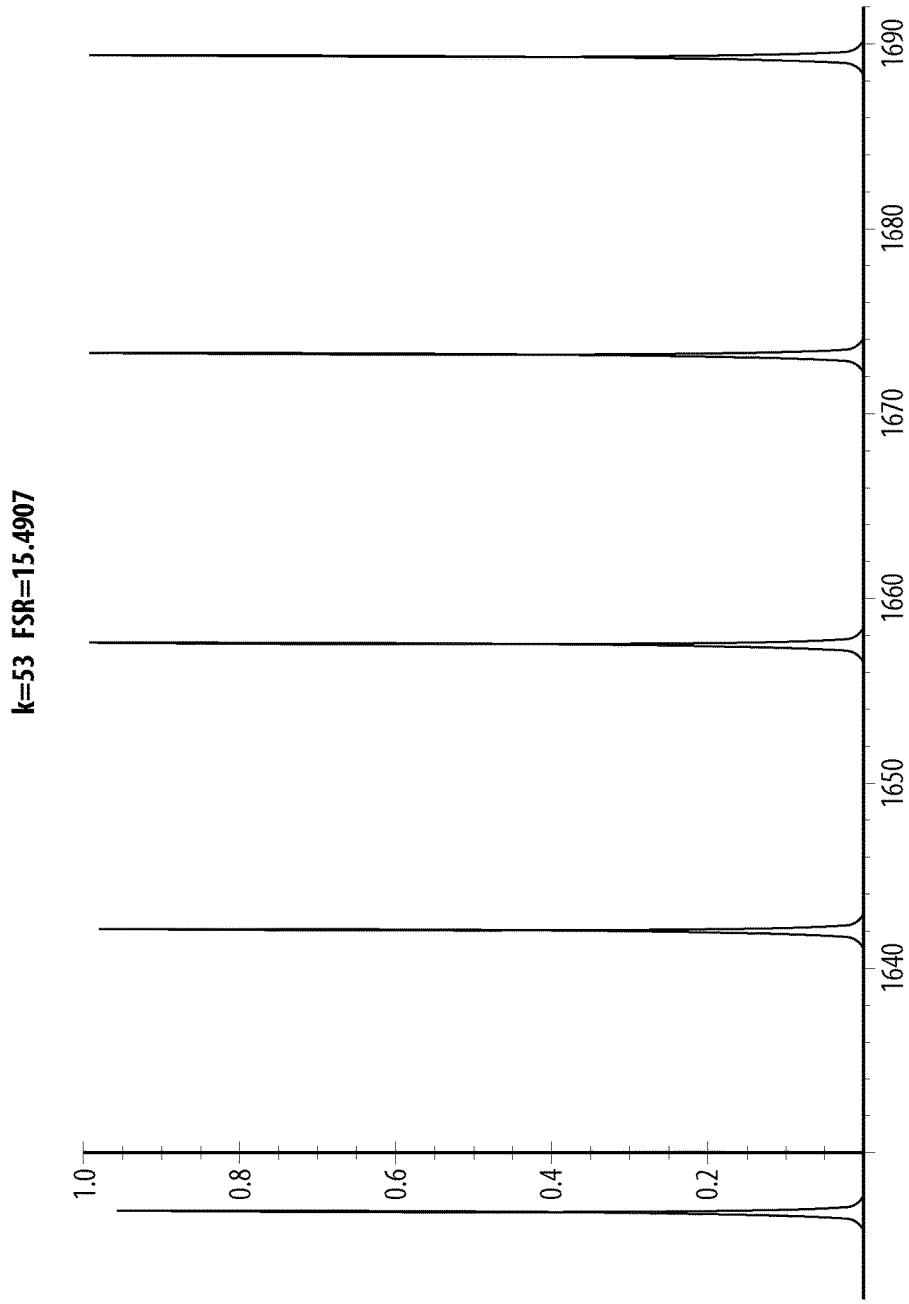
FIG. 5 is a plot showing the transfer function of a Fabry-Perot interferometer.

A Fabry-Perot interferometer can be seen as a combination of narrow bandpass filters whose center wavelengths are separated by a fixed amount (the FSR or free spectral range). The plot in FIG. 5 shows the transfer function of a Fabry-Perot interferometer. Each peak is called a mode. As is well-known to those skilled in the art, one characteristic of Fabry-Perot interferometers is finesse, a quantity related to the interferometer's mirror reflectivities and surface qualities.

The transfer function of a F-P interferometer is given by the following equation:

$$T(\lambda) = 1 / \left( \frac{4R\sin^2(2\pi\cos\theta n_s d/\lambda)}{(1-R)^2} - 1 \right)$$

where R is the mirror reflectivity (around 0.98), θ is the angle of incidence, d is the mirror spacing, $n_s$ is the gap index of refraction (for this application, this will have a value of 1 for a vacuum), λ is the wavelength of interest and T(λ) is the spectral transmissivity at the wavelength value of λ. In other words, if a signal having a box-shaped spectrum from $\lambda_1$ to $\lambda_2$ with a mean spectral radiance of α (expressed in [W/m²/sr/nm]) is presented, the output will have a spectral radiance of α×T(λ) (also expressed in [W/m²/sr/nm]). The peaks of that function are at λ=$dn_s$ cos θ/k where k c ℕ is the mode index.

Figure 6:
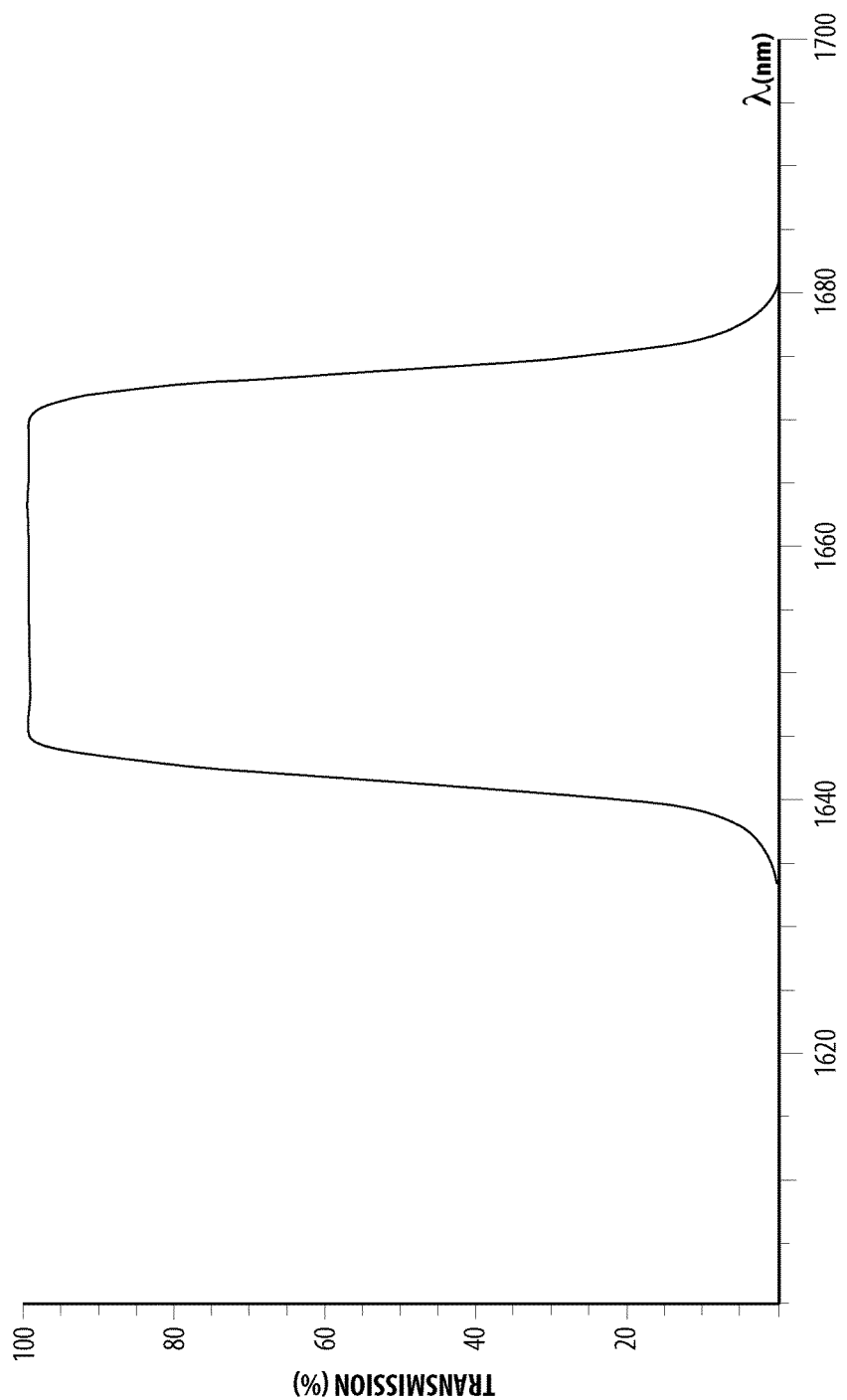
FIG. 6 is a plot of the order-sorting filter according to one embodiment of the invention.

Regarding the filter used with the invention, an order-sorting filter is used to select a subset of the available modes for the F-P interferometer. In one embodiment of the invention, two modes are selected. Referring to FIG. 6, illustrated is a plot of the order-sorting filter characteristic. It should be noted that if the order sorting filter only transmits a wavelength range corresponding to a single F-P mode with index k, then at an angle θ the peak wavelength will be $\lambda_0$=d $n_s$ cos θ/k. The equation above pertains to the case of ideal mirrors (with zero absorptive losses and perfectly flat, smooth surfaces). Straightforward generalizations exist to account for mirror imperfections.

The transmission function of the Fabry-Perot interferometer is a function of the optical path through it. Varying the angle of incidence causes a shift in the effective mirror spacing, causing a shift in wavelengths and a narrowing of both the FSR and the FWHM (full width at half maximum). When the interferometer is operating on collimated beams, different points of the field of view will be imaged at different effective spacings. If the order sorting filter only lets in a single mode, then the effect will be as if there is a different narrow bandpass filter for each pixel, with the central wavelength being a function of the radius from the optical axis. This effect is commonly referred to as a fringing pattern of concentric rings, where each fringe is at a different wavelength.

Figure 7:
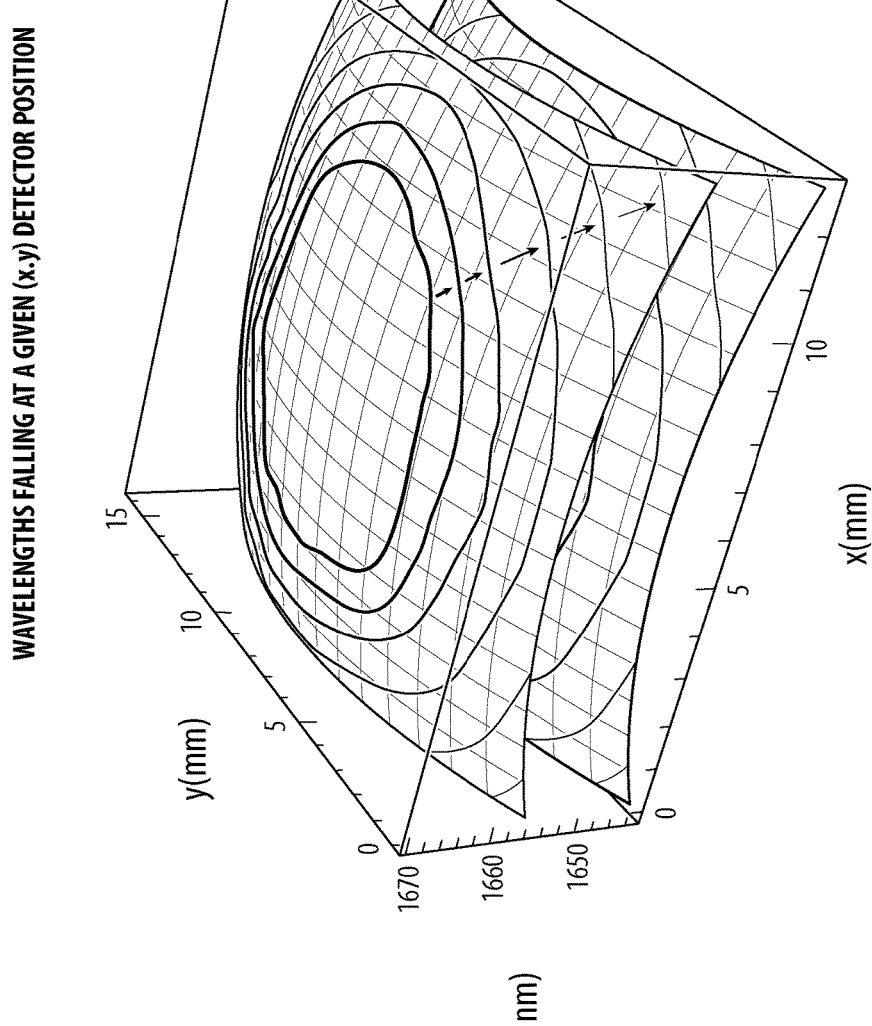
FIG. 7 shows, for each position on the image detector, the two or more wavelengths which fall on that position.

In one embodiment, the detector has a pixel pitch of 25 μm so that its active area is 16 mm by 12.8 mm. Taking one of the corners as the origin of a Cartesian coordinate system, FIG. 7 shows, for each detector position, the two wavelengths ($\lambda_1(x,y)$ and $\lambda_2(x,y)$) which fall on that position. The optical axis of the system falls on the center of the active region of the FPA (focal plane array) at coordinates $(x_0,y_0)$ =(8,6.4). It should be noted that the dimensions and characteristics of the detector are provided merely for illustration and should not be taken as limiting the scope of the invention.

Figure 8A:
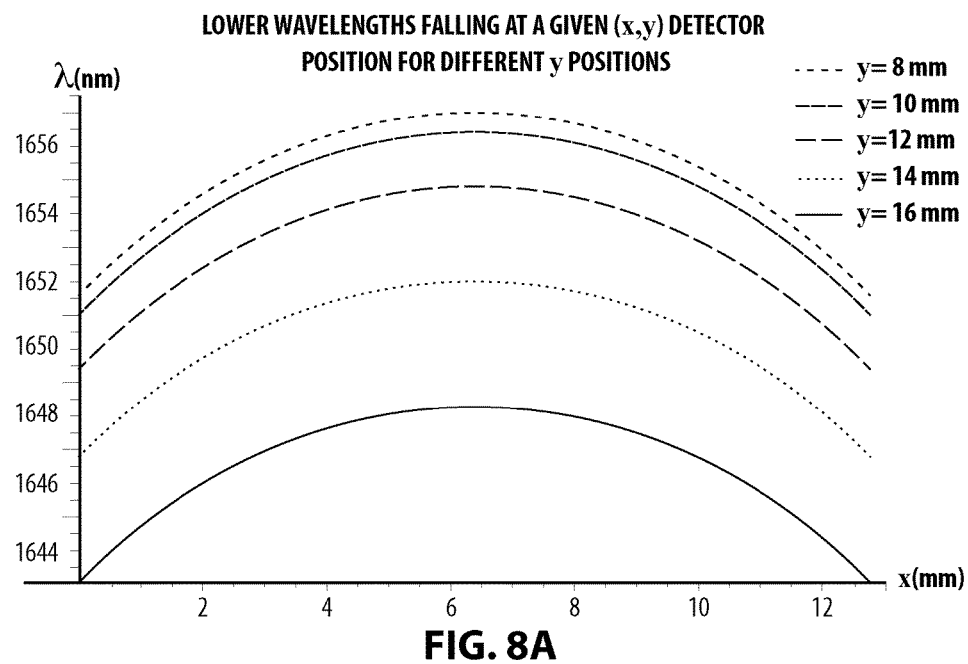
FIG. 8A illustrates the lower wavelengths falling on a given detector position for different y positions.
Figure 8B:
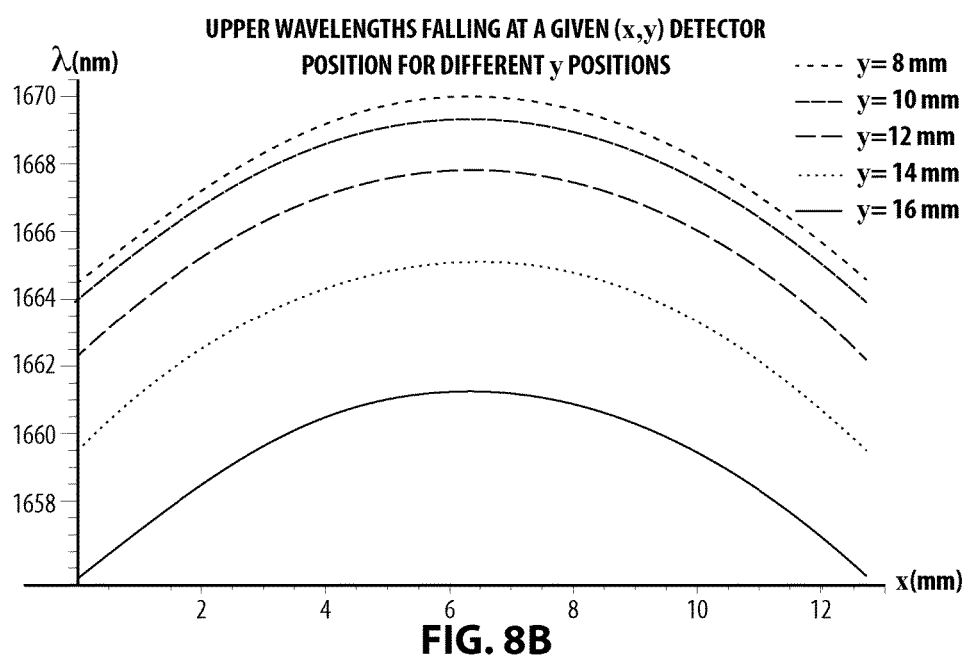
FIG. 8B illustrates the upper wavelengths falling on a given detector position for different y positions.

FIGS. 8A and 8B are provided to better explain the concept. As can be seen, FIG. 8A illustrates the lower wavelengths falling at a given (x,y) detector position for different y positions. FIG. 8B illustrates the upper wavelengths falling at a given (x,y) detector position for different y positions. It should be noted that multiple wavelengths (i.e. more than two wavelengths) are also possible for each detector position. Each detector position can have as many wavelengths as are passed through by the order sorting filter.

The optics for the system are designed such that from the center of the detector to one of its corners the collimated beam angle varies from 0° to a specified corner angle $\theta_{corner}$. In one embodiment, $\theta_{corner}$ is approximately 7.5°, but other values are possible. In the paraxial (small angle) approximation, light that falls at position (x,y) of the detector is obtained by focusing a collimated beam that traverses the F-P interferometer at an angle of:

$$\Theta(x,y) = \theta_{corner} r(x,y)/d_{edge}$$

where $d_{edge}$ is half the diagonal and the distance to the optical axis is given by:

$$r(x,y) = \sqrt{(x-x_0)^2 + (y-y_0)^2}$$

where $(x_0,y_0)$ are the coordinates of the detector point where rays traversing the Fabry-Perot with a zero angle converge.

In one implementation, the Fabry-Perot interferometer can be configured to have two adjacent modes that cover the wavelength regions from 1643.6 nm to 1656 nm (mode 1) and from 1656 nm to 1670 nm (mode 2).

In this case, spectral selection is achieved as a result of the angular wavelength shift and an order sorting filter which passes all wavelengths between 1643.6 nm and 1670 nm.

Spectral selection for the system is connected to spatial selection. Taking multiple images while a ground point is scrolling through the field of view will allow multiple spectral points to be acquired. During a pass of the satellite over the target area, the target area tracks across the field of view of the optical system, and data for multiple wavelengths is collected for each ground point in the target area.

In one implementation, the detector field of view has angles of 1.692° and 1.354° which will span a 19.2×15.36 km² area from an altitude of 650 km. The field of view is aligned so that the along-track direction is approximately parallel to its long edge.

Figure 9A:
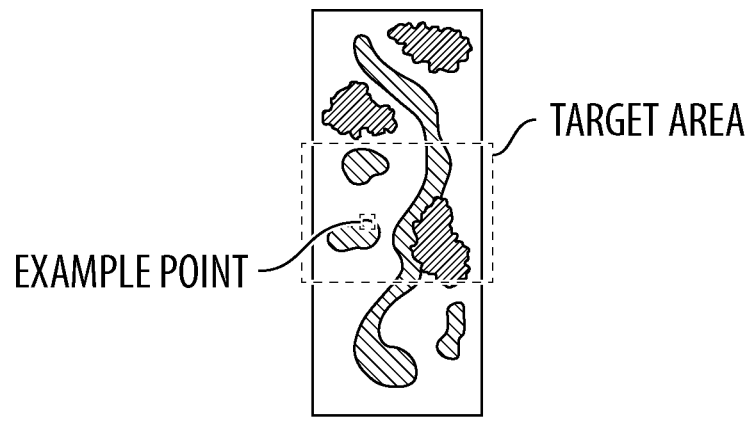
FIG. 9A illustrates the target area and its surrounding areas to show what the optical system is imaging.

The target area is defined as a 19.2×15.36 km² rectangle centered on a known target location. Without loss of generality it is assumed that the ground scrolls vertically in the field of view, from top to bottom. FIG. 9A illustrates the target area and its surroundings. Within the target area an example point has been selected.

Acquisition will start when the lower edge of the target area appears at the top of the detector frame. Frames will be then continually imaged until the upper edge of the target area reaches the bottom of the frame.

Figure 9B:
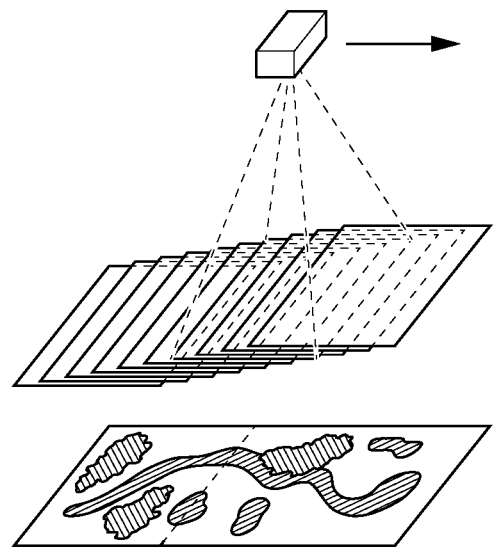
FIG. 9B is a schematic illustration of the satellite's path relative to the multiple images gathered.

In one implementation, the system is designed so that two hundred images, each with an exposure time of 100 ms, can be taken, allowing each target location to appear in at least one hundred images. FIG. 9B schematically illustrates the satellite and the overlap between these various images of the target location.

For exposure times of 100 ms, motion blur due to orbital motion and ideal panning is expected to degrade the along-track spatial resolution to 140 m, while the cross-track spatial resolution will stay at the nominal 30 m. Regarding pointing jitter, estimates are that pointing jitter will be significantly less than 100 arcsecond/s, which means that it will be at the subpixel level.

The trajectory of each target region point within the FPA (focal plane array) over the multiple images will be a function of the distribution of acquisition times and of the satellite attitude determination and control system. A simple linear trajectory model with equally spaced points is sufficient at this level, since pointing jitter will be negligible compared to other effects.

Figure 10A:
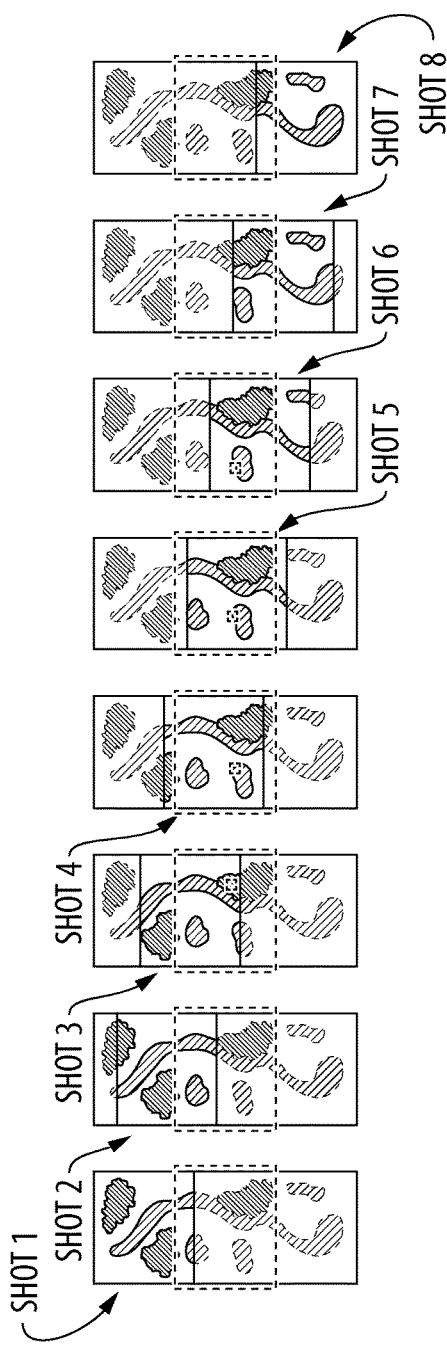
FIG. 10A show how the image gathered by optical system shifts as the satellite overflies the target location.

FIG. 10A illustrates how the target area will appear in different images. The target area is framed in a red rectangle, while the acquired area is highlighted. The acquired area moves downwards, causing the scene to scroll upwards in the acquired images. The image acquired at each stage of the process is illustrated in the series of images in FIG. 10B.

Figure 10B:
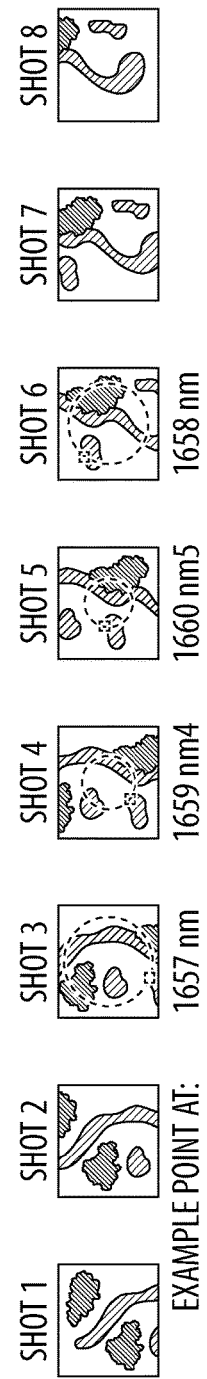
FIG. 10B illustrate the resulting image from the satellite's path over the target location.

In image 1 of FIGS. 10A and 10B, only a small part of the top of the target area is included in the acquired area. Images 4 and 5 capture most of the target area, and in image 8 only a small part of the bottom of the target area appears in the top of the acquired area.

The example point therefore has a linear, vertical trajectory within the field of view. It appears at different distances from the center of the field of view and thus at different pairs of wavelengths.

In image 3, the example point falls into a pixel where the Fabry-Perot interferometer lets in light with a wavelength at 1657±0.1 nm and with a wavelength of 1660±0.1 nm. In image 4, the interferometer lets in light with a wavelength of 1659±0.1 nm and light with a wavelength of 1672±0.1 nm, and so on (see FIG. 10B).

As can be seen from FIGS. 10A and 10B, multiple images are gathered by the imaging system as the satellite tracks the target area. To assist in the compression of the images, the various images can be aligned. As may be known, the largest variability of a top-of-the-atmosphere spectral radiance hypercube in the SWIR is the albedo or spectral reflectance of the ground locations. This quantity has low spectral dependence.

When gathering the multiple images, the scrolling of the field of view as a consequence of the satellite motion (natural motion combined with panning and jitter) produces a multitude of images which are slightly offset from each other. Aligning such a sequence of images greatly reduces the per-pixel variability, thus aiding compression. This alignment can be performed off-line using any number of tracking or optical stabilization algorithms, some of which have FPGA implementations. In effect, this alignment corrects the slanted sampling of the hypercube and allows traditional hyperspectral compression algorithms such as CCSDS-123 to perform at a much higher efficiency.

Another potential issue with the gathering of multiple images in a single pass is motion blur. Motion blur due to long exposure times can be partially compensated for by increasing the frame rate and by aligning groups of images before binning them. This will be limited by the maximum frame rate supported by the imaging sensor and the readout and quantization noises of said sensor. As the storage capacity and speed become limiting factors, an on-line algorithm can be preferable in some circumstances. Fortunately, working on small sets of images reduces the requirement for high accuracy and a simpler algorithm, implementable on an FPGA is adequate.

Figure 11:
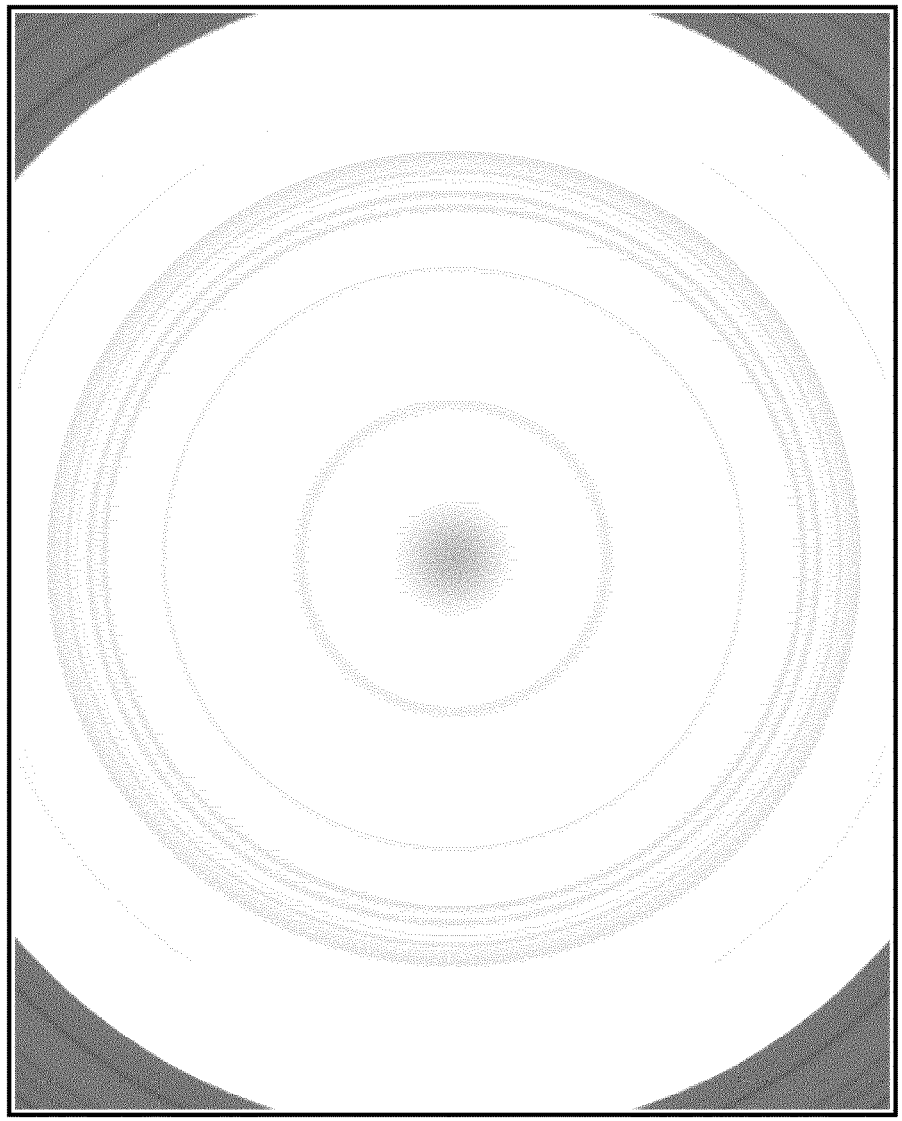
FIG. 11 shows how the optical system would image the top of atmosphere radiance spectrum over a constant albedo background.

Since the variation in the spectral reflectance of the surface of the Earth is very small over the narrow spectral range of the instrument, the average reflectance over that range, or albedo, is to be retrieved as a single parameter per ground pixel and is not expected to interfere significantly with the measurements. Since the optical system of the invention includes a wide-angle Fabry-Perot interferometer, absorption lines will cause the appearance of a fringing pattern of concentric rings. FIG. 11, illustrates how the system would image the top of atmosphere radiance spectrum over a constant albedo background. The spectrum was created using a MODTRAN 5 calculation for a 400 ppm $CO_2$ mixing ratio. In FIG. 11, each ring is an atmospheric absorption line. The circular edges are due to the use of an ideal boxcar model for the order sorting filter instead of a more accurate transfer function. These rings in FIG. 11 have a contrast of about 15%.

Figure 12:
FIG. 12 is a resulting satellite image with the various rings from FIG. 11.

FIG. 12 illustrates the resulting satellite image with the various rings shown in FIG. 11. In FIG. 12 the rings are quite faint and will not interfere with software implemented image registration methods. It should be noted that the albedo may have a smaller modulating effect on the image, thereby causing the contrast of the rings to be larger compared to the albedo. The rings should not be of such high relative contrast that they would interfere with image alignment algorithms by e.g. causing false features. The air-gap Fabry-Perot interferometer design has been selected to have very small thermal drift, so that the ring positions will be very stable across images. The ring pattern will therefore be well known and potential interferences with image alignment processes can be mitigated by excluding features that fall on known rings or by erasing the rings using image processing techniques.

The wide angle interferometer works using a measurement concept in which the input optics and the interferometer have a wide acceptance angle, such that the interferometer transmits a range of wavelengths. The central wavelength is imaged onto the center of the detector array with the wavelengths decreasing outwardly from the center in circles. The measurement of an atmospheric trace gas source on the Earth's surface using this arrangement uses several images (e.g. at intervals determined by the saturation level of the detector pixels, the gain, etc.), within each of which any selected ground point has a slightly different position in the field of view of the imaging system. The scrolling motion of the selected ground point across the field of view of the imaging system is a consequence of the orbital motion of the satellite, as adjusted by the satellite attitude determination and control system to optimize the number of images taken of each target area. This concept uses reference points on the surface (e.g. rapid changes of albedo) that can be used in post processing to co-register the different images, forming one measurement for each selected ground point with a high signal to noise ratio (SNR). The arrangement can also be used to simultaneously retrieve two or more atmospheric trace gas measurements.

The two examples given below illustrate the concept of simultaneously measuring both $CO_2$ and $CH_4$ emissions from a single point source (or target location) using the wide angle Fabry-Perot interferometer.

Figure 13:
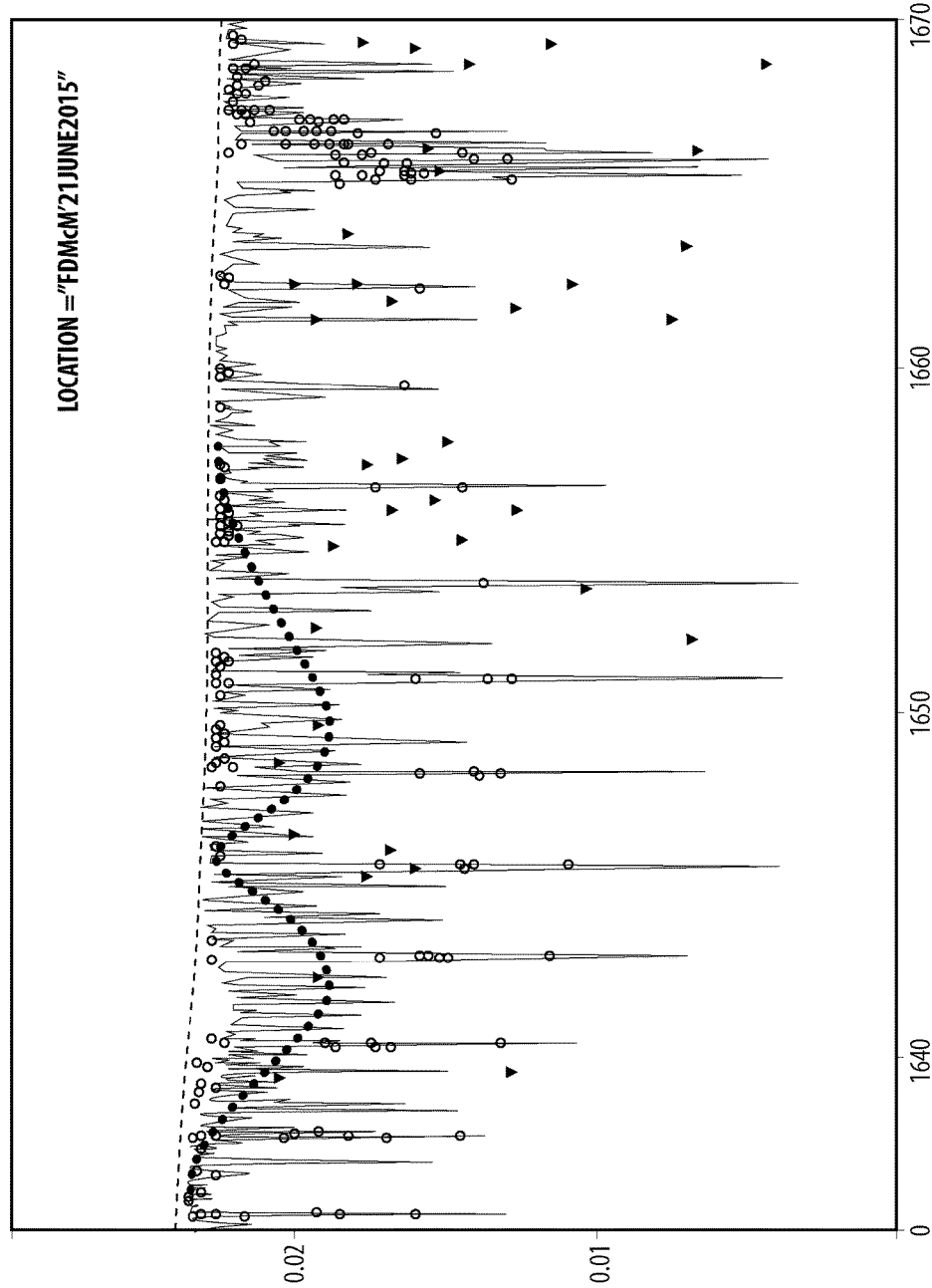
FIG. 13 is a plot for use in explaining the two example applications for one implementation of the invention.

Background information on the relevant spectral wavelength regions is shown in FIG. 13. In this and all following figures that show spectra, the vertical axis is radiance in $W/m^2/nm/sr$; the horizontal axis is wavelength in nm. In FIG. 13, the red, blue and green points show, respectively, the wavelengths and intensities of $CO_2$, $H_2O$ and $CH_4$ absorptions. The brown curve is a MODTRAN 5 calculation of the spectrum expected at this location and date, the dotted line is a very rough estimate of the top-of-atmosphere (ToA) radiance if the molecules were not present. The line intensities of the MODTRAN 5 and calculated spectra do not agree exactly because the line widths and mixing ratios for the two calculations were not exactly the same. This plot suffices, however, for the present purpose. As known to those skilled in the art, MODTRAN is a computer program used for modelling atmospheric propagation of electromagnetic radiation for the 0.2 to 100 um spectral range.

In the first example, the wide angle interferometer is used to simultaneously measure $CO_2$ and $CH_4$ emissions. One possible range which may be used is the band between about 1635 and 1645 nm and for which the focus would be on the $CO_2$ R-branch. This wavelength range also contains four strong $CH_4$ multiplets but this region is not the best region for the measurement of $CH_4$. The range between about 1645 and 1670 nm is a much better range for measuring $CH_4$ emissions. This better choice range also contains the $CO_2$ P-Branch corresponding to the R-Branch previously considered. There are more interferences between $CO_2$ and $CH_4$ and $H_2O$ lines in this 1645-1670 nm region, so it was not selected in the past, but many of the $CH_4$ lines—the most important interferences—are weak and could possibly be accounted for in the retrieval, in view of the fact that $CH_4$ itself is being retrieved.

Figure 14:
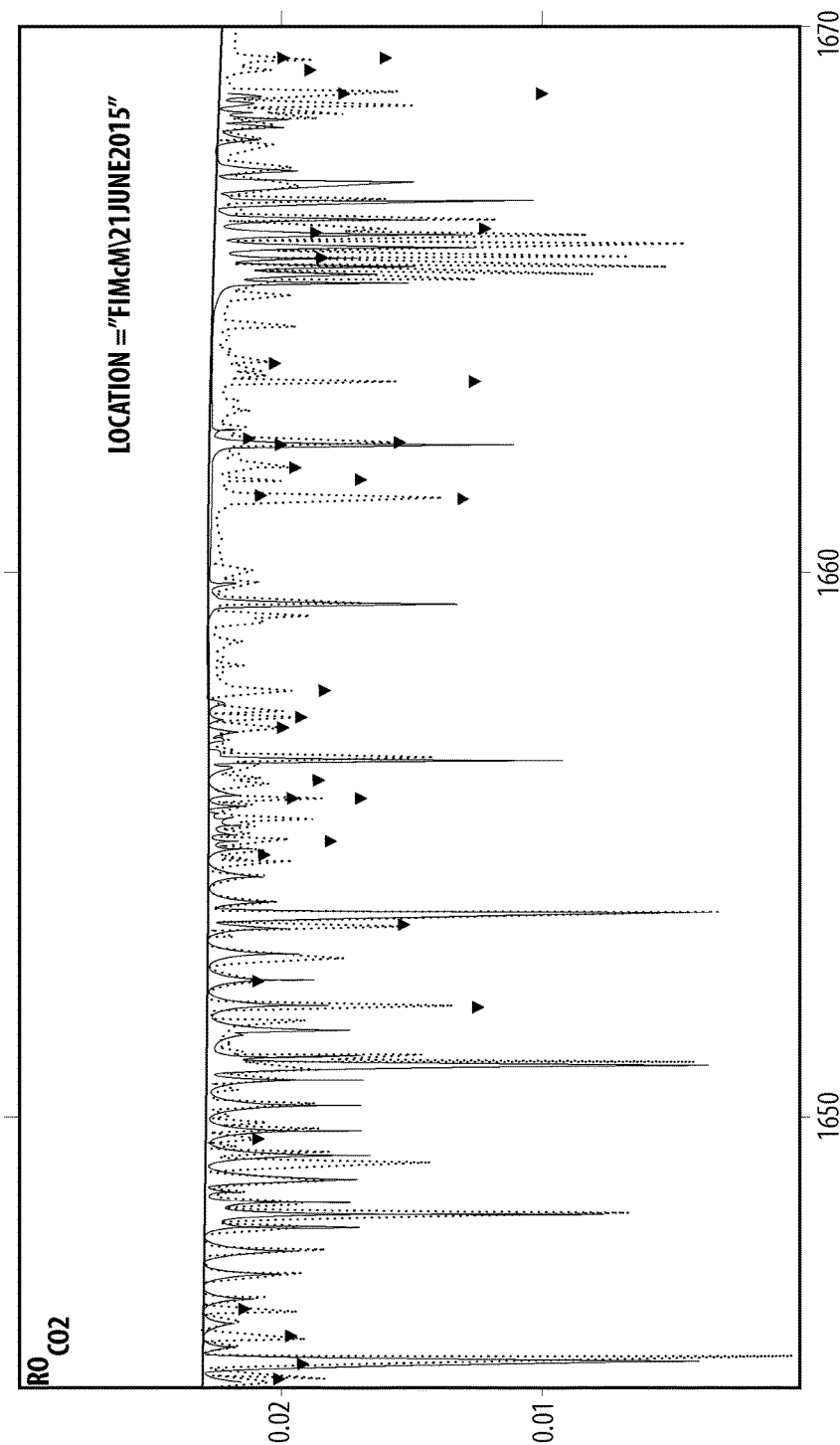
FIG. 14 is a plot covering the region between 1645 nm and 1670 nm when used for a wide-angle Fabry-Perot interferometer measurement.

With this in mind, the region between 1645 and 1670 nm is used as a candidate for wide angle Fabry-Perot (WAF-P) measurement in FIG. 14. Here, the red curve is the spectrum of all $CO_2$ and $CH_4$ transitions falling in the target wavelength range (calculated with Voigt absorption line profiles). The dotted curve is the same MODTRAN calculation shown in FIG. 13. The blue points are $H_2O$ transitions. This shows the fact that both (relatively) high and low rotational transitions of both molecules are present in the spectra. This is required if temperature measurements are to be made. The strong cluster of lines near 1665 nm is the $2v_3$Q-Branch. The 7 strong lines to the left of this feature are the lowest rotational transitions of the corresponding R-branch. In both cases the lines exhibit fine structure (they have increasing numbers of sub-levels for each transition), but the spectroscopy of this is well known.

Figure 15:
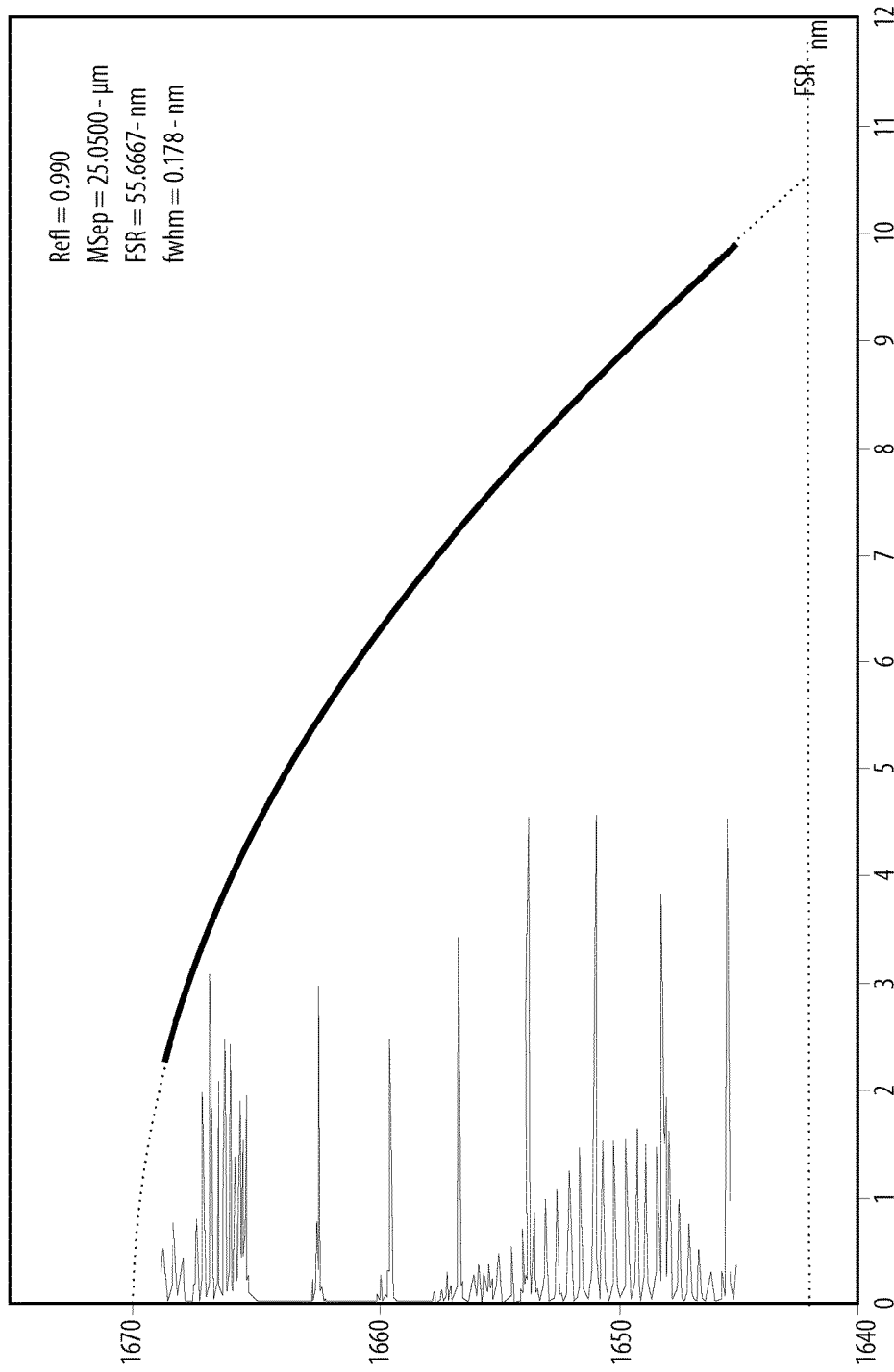
FIG. 15 plots the range of 1645 nm to 1670 nm against an interferometer acceptance angle from 0 to 11 degrees.

In one implementation of the invention, if the entire wavelength range between 1645 and 1670 nm is to be measured by the WAF-P technique, the range of acceptance angles must be from 0 to about 11 degrees. This is shown in FIG. 15, in which the vertical axis is wavelength (nm) and the horizontal axis is the F-P interferometer acceptance angle (in degrees). The blue curve is the spectrum shown in FIG. 14. The red curve is the maximum of the interferometer transmission for light that is incident at the indicated angle. The dense black dots show the intersection of the wavelengths of the spectral lines with this curve. $FSR_{lim}$ shows the wavelength range of ½ FSR (free spectral range), beginning at the (assumed) central wavelength of 1670 nm. The interferometer parameters chosen for this simulation are shown in FIG. 15. These interferometer parameters are, of course, arbitrary, but they must satisfy two criteria: the interferometer FWHM (full width at half maximum) must be narrow enough to achieve a pre-defined resolution limit. For this situation, the pre-defined resolution limit was assumed to be about 0.1 nm (see below) and the FSR must be wide enough to permit transmission of the desired wavelength range.

Figure 16:
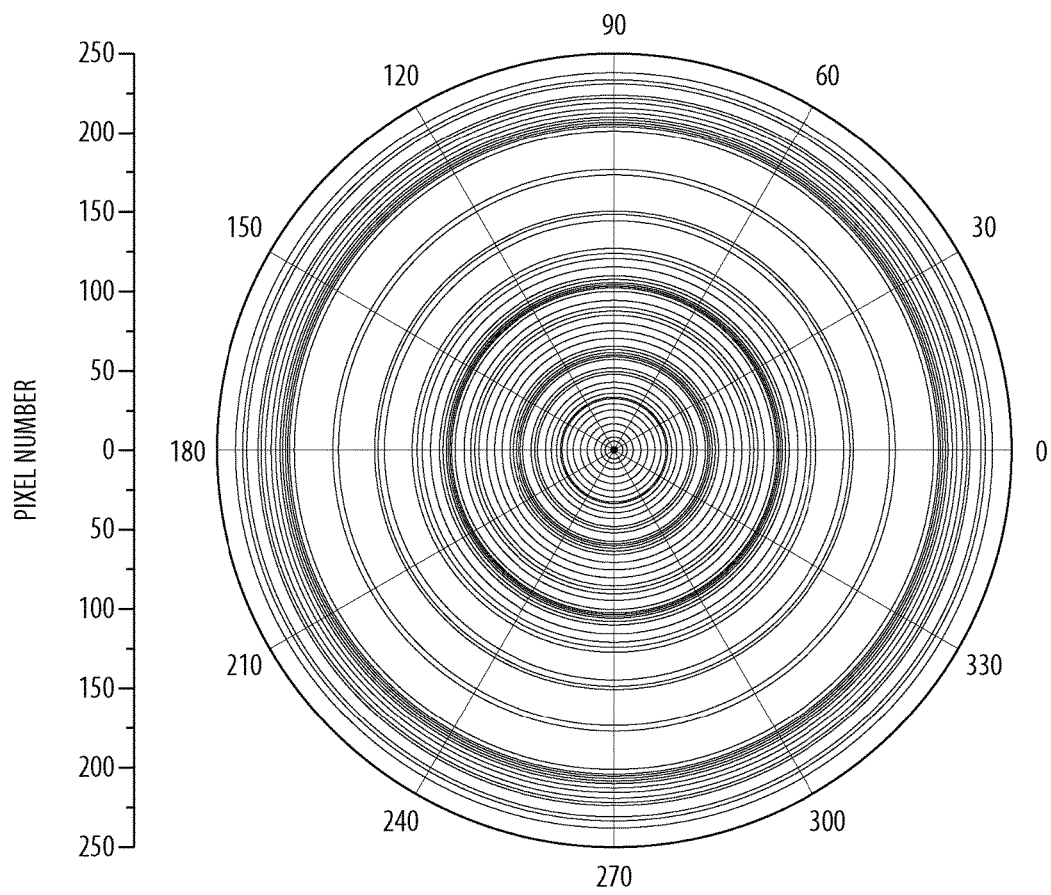
FIG. 16 illustrates a plot of the spectrum in FIG. 14 imaged on to 500 pixels of the detector using the projection used in FIG. 15.

The spectral resolution in a WAF-P measurement is limited by two things: the interferometer's FWHM (full width at half maximum) and the pixel pitch of the array detector. This is illustrated in FIG. 16. Here, the spectrum shown in FIG. 14 is imaged onto 500 pixels of the detector using the projection shown in FIG. 15. The central pixel is at 1645 nm while the extreme pixels are at 1670 nm. Each circle is located at the centre of one of the lines in the spectrum. For example, the group of circles with radii between about 200 and 225 pixels are the transitions in the $CH_4Q$-branch. The two groups of circles at approximately 175 and 150 pixels are the $CH_4R_0$ and $R_1$ transitions respectively, and so forth. A wavelength range of 25 nm has been imaged onto ½ of a 512 pixel detector, so the wavelength resolution is 0.1 nm/pixel. This corresponds roughly to the wavelength limit set by the interferometer FWHM.

The spatial resolution of the invention is determined by the parameters of the imaging system and the camera. The distance on the ground corresponding to one camera pixel is referred to as the ground sampling distance (GSD), and, in one embodiment, its value is 30 meters. The spatial resolution is fundamentally limited by diffraction (this limit is determined by input aperture size, optical wavelength and distance of the instrument from the object plane). In practice, however, effects such as aberrations typically increase the spatial resolution above the diffraction limit. If the spatial resolution is smaller than the GSD, then the latter quantity ultimately determines the ability to resolve closely spaced objects on the ground. This also pertains to the instrument's ability to characterize the spatial variations of trace gas concentrations (in other words, the detailed shape of an emissions plume).

Figure 17:
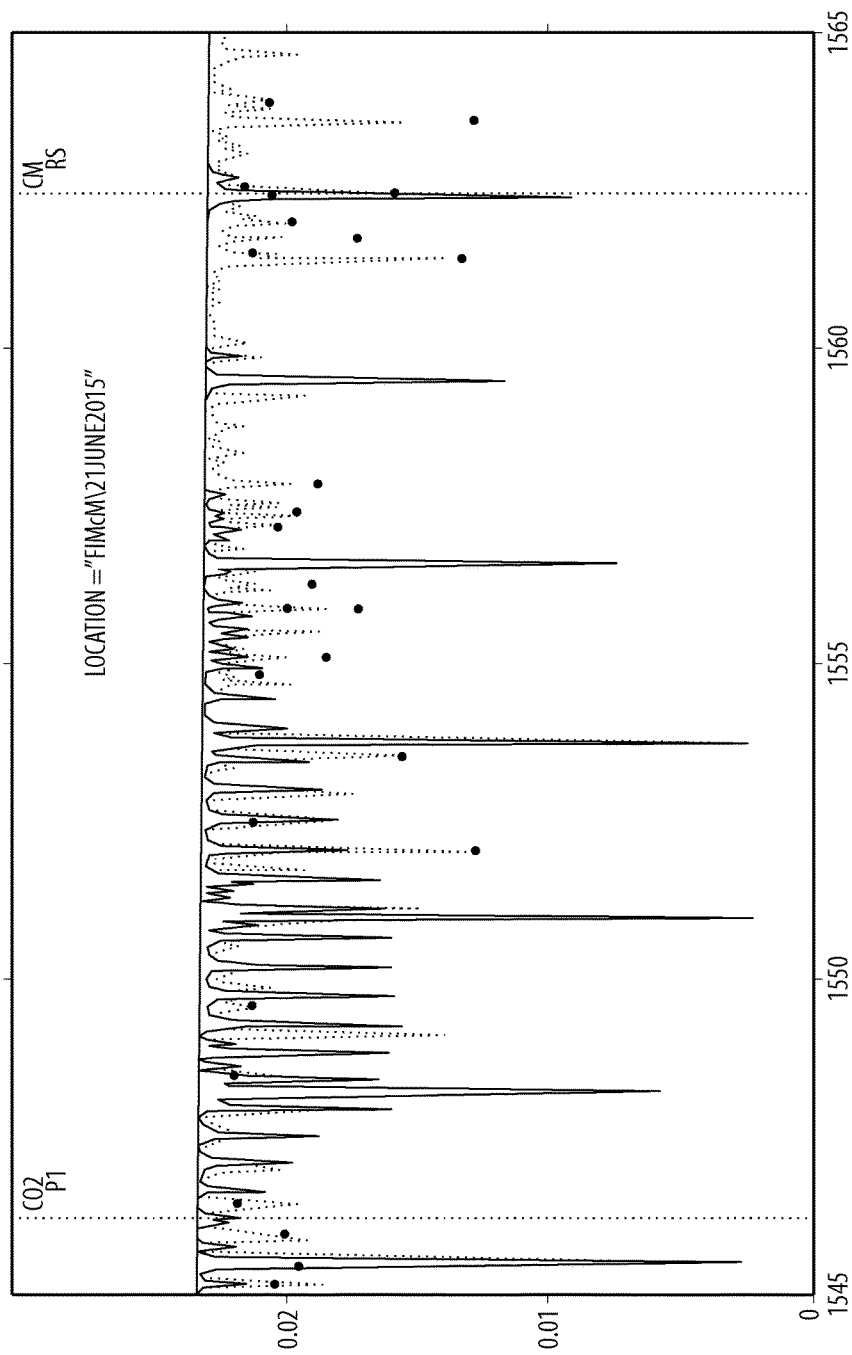
FIG. 17 shows the spectra from FIG. 14 plotted against a wavelength range from 1645 nm to 1665 nm.
Figure 18:
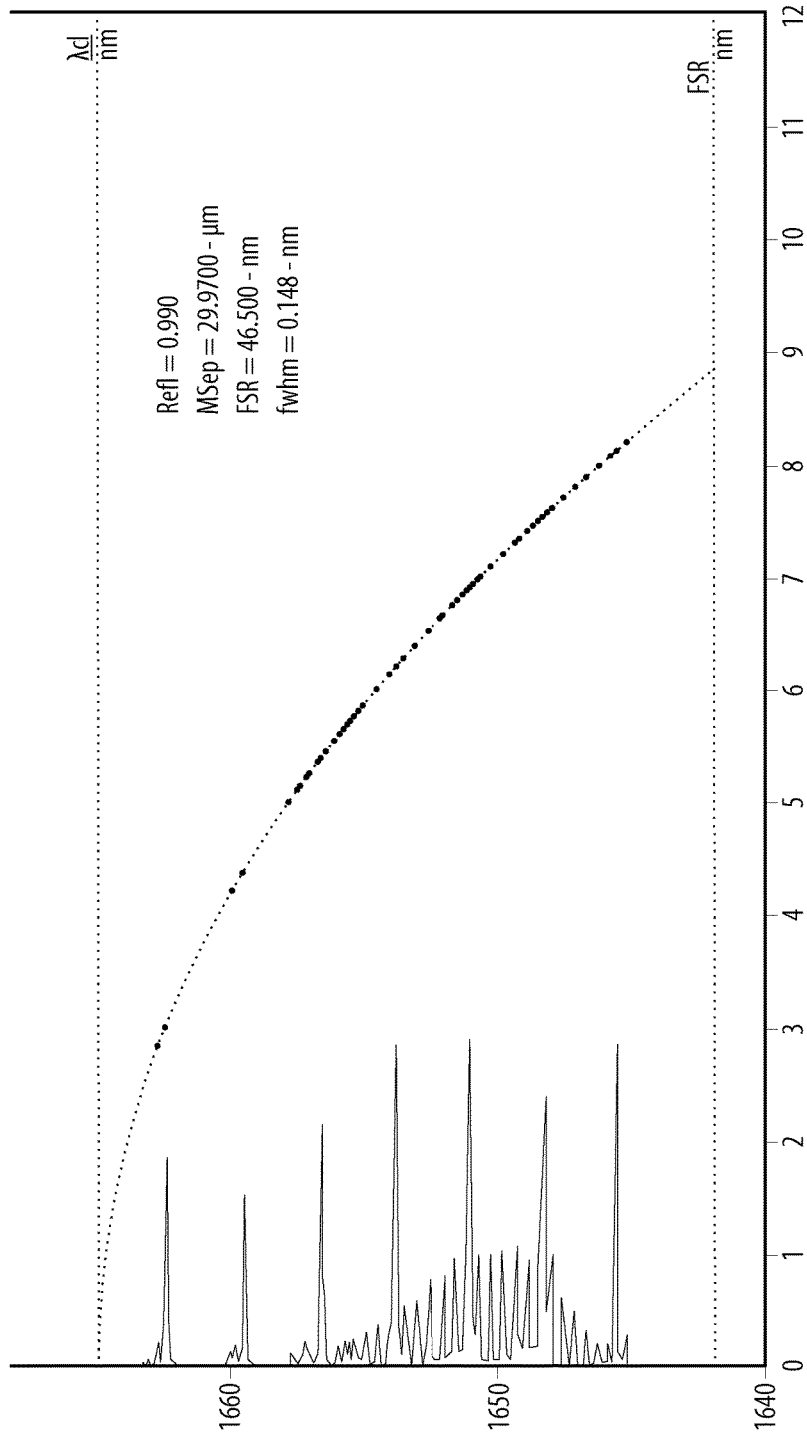
FIG. 18 plots the maximum interferometer transmission as a function of acceptance angle with the transmission being from 1640 nm to 1665 nm and the acceptance angles being from 0 to 11 degrees.
Figure 19:
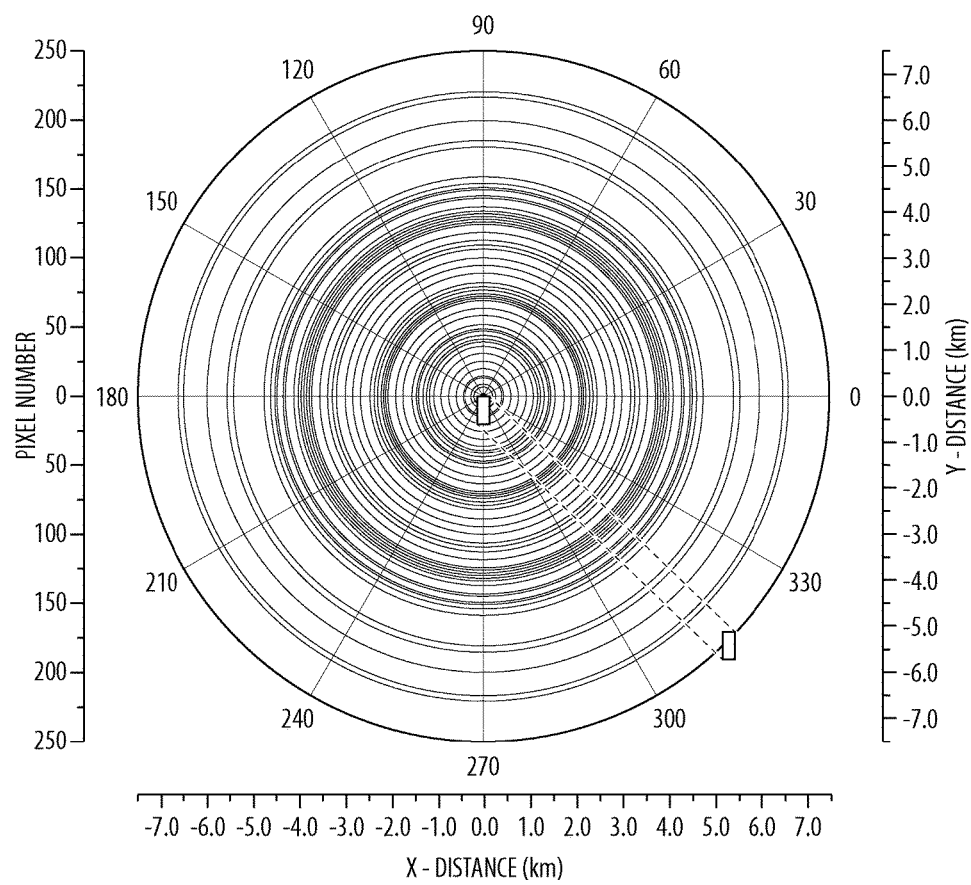
FIG. 19 is a fringe plot for the wavelength range in FIG. 18.

In the second example, FIG. 17 shows the spectra from FIG. 14 in a slightly smaller wavelength range (from 1645 nm to 1665 nm). This 20 nm range covers all of the $CO_2P$-Branch that is populated at room temperature and also the first 7 transitions in the $CH_4R$-Branch. The corresponding F-P interferometer parameters and range of acceptance angles is shown in FIG. 18. The red curve in FIG. 18 shows the maximum F-P interferometer transmission as a function of acceptance angle while the black dots indicate the wavelengths of the strong lines in the spectrum. The fringe plot for this wavelength range is shown in FIG. 19. In this case, the $CO_2P$-Branch lines are the fringes starting at the centre point. The fringes with increasing diameters are P-Branch lines with increasing rotational quantum numbers. The two isolated multiplets near pixel numbers 225 and 175 are the two lowest rotational states of the $CH_4R$-Branch.

It should be noted that the red rectangles in FIG. 19 show the size of a 300 m×600 m object. This is meant to represent the approximate area covered by the dense part of a plume from a single point source. The dashed lines represent the possible scrolling of such a target area across the field of view of the imaging system over the duration of a satellite pass. The trajectory in this example passes through the centre of the field of view and intersects all of the fringes—an idealized condition to maximize the number of spectral lines sampled for the source or target. In one implementation of the invention, if twenty-five 200 ms measurements are recorded during a 5s overpass, these images would be separated spatially by approximately 300 m, forming a near-continuous spatial record of the source emission.

To assist in the data processing of the images gathered by the satellite, some of the processing may be performed on the satellite. Since the communications bandwidth available to nanosatellite platforms tends to be severely limited, with typical values being in the tens of megabytes per day, and since hyperspectral imaging produces high data volumes in the hundreds of megabytes per target, transmitting the data to an earth station for processing may not be advisable.

In one embodiment of the invention, low-power embedded processors located on the satellite, are used to reduce the high data volumes produced into much smaller ultimate data products such as concentration maps. These processors, optionally endowed with reconfigurable logic (in the form of FPGAs or field programmable gate arrays), when deployed on the satellite, provide an alternative to having to transmit large volumes of data to a ground station for processing. Instead, on-board processing can occur and much smaller data sets can be transmitted to the ground station.

To retrieve the spectral response at each point on the above maps, a software implemented image registration method is used to determine, for each ground pixel G having ground coordinates $(u_G, v_G)$ and each frame k, the detector position $(x_{G,k}, y_{G,k})$ where G appears in frame k, and thus the radius from the optical axis, and therefore the Fabry-Perot (FP) traversal angle corresponding to calibrated wavelengths. In frame k, let $z_{G,k}$ be the value of the pixel at detector position $(x_{G,k}, y_{G,k})$. It is possible for the ground pixel to not appear in certain frames due to irregularities in the motion of the field of view, or the presence of obstructions on the detector such as dark masks used to measure the dark current. Let $O_G$ be the number of frames where the ground pixel G appears at an active detector pixel, and let $k_1 < \ldots < k_{O_G}$ be the indices of the valid frames. Note that the spectral response of a detector pixel $(x_{G,k}, y_{G,k})$ only depends on the angle of traversal of the Fabry-Perot $\theta_{G,k} = \theta(x_{G,k}, y_{G,k})$ where $\theta$ is $\Theta(x,y) = \theta_{corner} r(x,y)/d_{edge}$ as defined above. Thus the spectral information about ground pixel G is given by the set of quadruplets $R_G = (u_G, v_G, \theta_{G,k_h}, z_{G,k_h})$ for $1 <= h <= O_G$, where $(u_G, v_G)$ are the ground coordinates, $\theta_{G,k_h}$ is the spectral parameter in the form of a signed Fabry-Perot angle (whose absolute value in the case of a single-mode instrument is in one-to-one relationship with a peak wavelength) and $z_{G,k_h}$ is the integrated radiance value measured for the detector pixel at which the ground pixel G appears in frame $k_h$. We call this set the response of the detector to ground pixel G.

Taking the union, for all target ground points G, of the responses $R_G$ yields a non-uniform sampling of a multi-mode spectral hypercube R. This is a collection of quadruplets $(u,v,\theta,z)$ that may be interpolated using (as an example) linear interpolation into a function $R(u,v,\theta)-z$ which is a multi-mode spectral response hypercube. In the single mode case this is identical to the classical notion of a hypercube. In the n-mode case this can be viewed as a sum of n hypercubes where the wavelength coordinate of each hypercube is shifted by one FSR. Of course, other interpolation methods and schemes may be used to arrive at the multi-mode response hypercube.

To determine the vertical column densities of atmospheric trace gases, the parameters of a predetermined forward model are recursively adjusted and the results of the model from the adjusted parameters are compared to the measured responses. Then, when the difference between the results from the model and the measured responses are at a minimum, the parameters used to arrive at the model results are determined to be the vertical column densities for the various atmospheric trace gases. The details of this process are provided below.

Within a given scene, the global atmospheric conditions are assumed to be known and local atmospheric conditions are modeled using P parameters such as two spectral reflectance parameters (average and slope), vertical column densities for the different gases ($CO_2$, $CH_4$, $H_2O$). For each pixel ground pixel (u, v), a tuple ($p_1, \ldots, p_P$) of atmospheric parameters is guessed and the expected top-of-the-atmosphere spectral radiance (TOASR) $\lambda$ is calculated using a forward model such as MODTRAN 5. The set of FP angles ($\theta_i$) at which the ground pixel (u,v) has been acquired is known. For each such angle, the FP transmittance at that angle is multiplied with the TOASR $\lambda$ and the result is integrated by taking into account the order-sorting filter response, the spectral response of the optics and the quantum efficiency curve of the sensor to arrive at an expected response $e_i$. The collection of expected responses ($e_i$) is compared to the collection of measured responses ($z_i$) which include measurement noise. The parameters are adjusted until the discrepancy between the expected response and the measured response is minimized. This forms a numerical optimization problem that can be addressed by established techniques.

The plume would be identifiable in many pixels. The total concentration, obtained by adding the source plus background concentrations, would be obtained from these pixels. The corresponding absorption by the background column would be obtained from the pixels outside the source region. The effects of local variations in albedo on the measurement would be reflected in the variations of apparent absorption on the circumference of each circle. Albedo variations at other locations in the field of view would also be useful for such things as the location of surface features that could assist in scene registration.

For more clarity on how to determine a concentration of a plume as noted above, it should be noted that one of the goals of the present invention is to measure source fluxes. Fluxes manifest as plumes or as combinations of plumes. These are high-spatial variability excess VCD (vertical column density) patterns above the low-spatial variability but with an unknown background spectrum.

Modeling of the background spectrum from a knowledge of the background atmospheric parameters is not necessary if the background spectrum can be measured from the scene itself. And, because plumes are localized (they are only expected to occupy a fraction of the field of view), their origins can be known since prior knowledge of the ground location of the emitting sources can be assumed. This is because it will be possible to geo-reference SWIR images. No source is expected to be large enough to significantly affect the vertical column density (VCD) levels of the whole field of view.

A simple spectral absorption map centered on one or more of the transition lines of the gas of interest will provide a visible map of the plume shapes. This, combined with a knowledge of the local wind direction history, makes it possible to partition, either manually or automatically and without further modeling, the ground pixels of the acquired imagery into two subsets: background and foreground.

As the atmospheric conditions are assumed to be constant or slowly varying amongst locations classified as background locations, the spectral radiance emanating from these background points will be equal up to a multiplicative factor caused by the location-specific albedo. The background spectrum can therefore be assembled for these points by a least-squares fit of these samples, and then extrapolated to the totality of the scene. This provides the background spectra for the foreground pixels.

The spectral effect of the emitted plumes can be modeled as an independent multiplicative effect over the background spectrum. Thus, in the single mode case, by dividing the observed foreground spectra by the extrapolated background spectrum of the foreground pixels we get the absorption spectrum of a layer of target gases multiplied by the spectral reflectance.

The excess VCD for a given foreground location can therefore be retrieved by forward spectral modeling a layer of target gases to fit the observed absorption spectrum, thereby avoiding the complexities of atmospheric modeling.

To further reduce the amount of data to be transmitted to a ground station, selective binning can be used. Binning of detector channels (e.g. pixels) will cause a degradation of spectral resolution unless only spectrally equivalent pixels are binned. In the system of the invention, spectral equivalence classes are circles centered around the null point of the detector (i.e. the point where the optical axis falls.) Spectrally coherent binning can be performed by the payload to reduce the data volume.

Projecting the data to a smaller space is a standard numerical analysis operation that typically results in great data reduction, as the reduced data may be sufficient to perform a subsequent fit. The reduction operator is typically linear, independent of the target data set and can be a set of spectral kernels, or a basis of wavelets. The reduction kernels can therefore be pre-programmed and the processing modules aboard the satellite can perform the data reduction operation.

Once the data have been reduced, only the reduced vectors are downlinked or sent to the ground station. The algorithmically complex, non-linear fit operation can be performed on the ground.

To ensure that the correct target area is being imaged, "thumbnails" or smaller versions of the images obtained can be transmitted to a ground station before a full resolution image of the target area is transmitted. The issue is that the targeting error of a nanosatellite platform may amount to a significant fraction of the field of view, thereby limiting the maximum unclipped target size. Target sites also come in varying shapes and sizes and, as such, only a portion of the reassembled field of view will contain the target site. However, limiting the downlinked data (or data transmitted to a ground station) to the useful portion requires knowledge of the target location within the acquired images. This is best determined semi-automatically by operators comparing the acquired imagery with known, geo-referenced imagery. To this end, a limited version of the acquired imagery can therefore be first transmitted. This "preview" version can be limited in spatial or spectral resolution or dynamic range. Ideally, the data volume should fit into a single pass. The operators can then correlate the preview version with known imagery, select a region of interest comprising the target, and transmit a description of that region of interest to the satellite data processing assets. The satellite on-board data processors can then produce a cropped dataset based on that region of interest and this cropped dataset can then be transmitted to the ground station.

As an alternative, it is also possible to produce a set of small visual descriptors of the target area based on existing imagery. These visual descriptors can be uplinked to the satellite data processors and the descriptors can be used to automatically select and crop the region-of-interest. As a further alternative, the on-board processors can be programmed to automatically trigger acquisition of a specific region once the uplinked descriptors have been detected.

Regarding the Fabry-Perot interferometer, to obtain a large aperture and a high finesse, a number of techniques were used.

As noted above, the present invention uses a Fabry-Perot interferometer (FP) with an imaging system to obtain spectral information. Most high finesse Fabry-Perot interferometers are composed of 2 curved mirrors. These two mirrors are used as the resonance cavity.

In the imaging system of the invention, the angle at which light enters the FP interferometer changes the resonance frequency of the cavity. This enables us to obtain the atmosphere's spectral information in the form of rings on the detector as explained above. With curved mirrors, the FP interferometer is only resonant for discrete spatial modes, thereby making it no longer possible to image through the interferometer. Because of this, a plane-parallel cavity is used, even if a high finesse can be harder to obtain. Furthermore, in order to obtain sufficient signal to retrieve the spectral information from the images, the clear aperture of the FP interferometer has to be quite large (in one implementation, it is 22 mm). With the combination of both a high finesse and a large clear aperture, the FP interferometer of the invention is unique.

The finesse of the FP interferometer is a combination of the reflectivity finesse and the defect finesse. The reflectivity finesse is controlled by the reflectivity of the mirrors. In one implementation of the invention, the FP interferometer uses two mirrors with a reflectivity of 97.7% and this gives a reflectivity finesse of 135. The defect finesse is controlled by the surface roughness and surface curvature of the two mirrors as well as the surface tilt between the mirrors. The expected defect finesse in this implementation is 197.5 (at 1652.5 nm). This defect finesse over the whole clear aperture is extremely high.

Preferably, the surface match between the two mirrors is controlled in order to have near perfect surface roughness (below 1 nm rms), surface curvature (below 2 nm) and surface tilt (below 2 nm). The high finesse of the Fabry-Perot interferometer of the invention is obtained using a combination of techniques as explained below.

One technique uses fluid jet polishing to obtain very a good surface match between the two mirrors. For this technique, the fused silica substrates are initially polished to have a surface quality of $\lambda/20$. Once that is obtained, the FP interferometer is assembled and the optical transmission is measured so that the gap spacing between the two surfaces can be obtained. Once the gap spacing is obtained, one of the two surfaces is polished using a fluid jet polishing technique in order to get a near perfect match between the two surfaces. That process is iteratively repeated until a surface match of about $\lambda/600$ between the two mirrors is obtained. With this technique, the surface roughness and surface curvature can be controlled to the desired values.

Another technique used is that of pre-compensating for the predicted mechanical stress caused by the mirror coating. In this technique, before the mirror coating step, the substrate might be flat, but the mechanical stress produced by the coating can cause the substrates to curve on the nanometer level. In order to correct for that curvature, two substrates were coated with the same thickness and material as the desired mirror coating. The value of the curve was then measured. Using this value, the substrates for the FP interferometer are then polished to have the inverse curve prior to the coating step. Using this technique, single digit nanometer curvatures can be obtained.

A further technique involves a fine-tilt adjustment using a mechanical mount for the FP interferometer. In this technique, once the fluid jet polishing and the pre-compensation have been accomplished, the tilt between the two mirrors still remains to be corrected. A mount is designed for that reason. Three flexures apply pressure on the FP interferometer assembly in relative amounts so that the tilt between the mirrors becomes, in one implementation of the invention, smaller than 2 nm over the whole aperture.

As noted above, the various aspects of the invention may be implemented as a system or as parts of a larger system. Some aspects of the invention may be implemented as being part of a larger monitoring system involving an aerial platform (e.g. a manned or unmanned aerial vehicle) or a satellite. While the above examples illustrate an embodiment where various aspects of the invention are mounted on a satellite, these aspects may also be mounted on a suitable aerial platform. Such an embodiment may differ from a satellite implementation in the type/capability of the telescope used.

It should also be noted that while the above examples disclose using the invention for specific spectral ranges, spectral ranges other than those mentioned above are also possible. As another example, the present invention may be used for the 350-450 nm range as well as for the 200 nm to 20 micron range. These ranges are provided only as examples and should not be taken as limiting the scope of the invention.

The embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g. "C") or an object-oriented language (e.g. "C++", "java", "PHP", "PYTHON" or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A system for detecting atmospheric trace gas emissions from a specific target location by way of an observation platform, the system comprising:
   an image gathering device located at said platform, said platform being for overflying said specific target location, said image gathering device being for gathering multiple images of said specific target location as said platform overflies said specific target location;
   a Fabry-Perot interferometer having a range of angles, said interferometer being located at said platform and being configured such that light gathered from said specific target location passes through said interferometer before being received by said image gathering device; and
   a filter for filtering light from said specific target location prior to being received by said interferometer, said filter being for allowing multiple modes in a selected spectral range to pass through said filter to said image gathering device;
   wherein said Fabry-Perot interferometer comprises at least two mirrors, each of said at least two mirrors having the following characteristics:
   a surface roughness of less than 1 nm rms;
   a surface curvature of less than 2 nm; and
   a surface tilt of less than 2 nm.

2. A system according to claim 1 wherein said multiple modes allowed by said filter to pass through are modes adjacent to one another.

3. A system according to claim 1 further including data processing modules on-board said platform, said data processing modules being for image processing said multiple images, said multiple images being processed prior to being transmitted to a ground station.

4. A system according to claim 3 wherein said data processing modules process said multiple images to thereby transmit a reduced resolution image from said multiple images to a ground station and to thereby receive target data from said ground station in response, said target data being indicative of said specific target location to be imaged by said image gathering device.

5. A system according to claim 4 wherein said target data is used by said data processing modules to determine which parts of which images of said multiple images are to be transmitted to said ground station.

6. A system according to claim 3 wherein at least two of said multiple images are processed by said data processing modules to thereby align said images with one another prior to compressing said multiple images.

7. A system according to claim 3 wherein said multiple images are processed by data processing modules to produce concentration maps.

8. A system according to claim 1 wherein said Fabry-Perot interferometer is produced using at least one of:
   a fluid jet polishing technique for obtaining a suitable match between two surfaces of mirrors used in said interferometer;
   pre-compensating for expected curvatures due to coatings on said mirrors;
   adjusting a tilt between said mirrors by using a plurality of flexures which apply pressure in relative amounts to reduce said tilt.

9. A system according to claim 1 wherein said Fabry-Perot interferometer uses a plane-parallel cavity.

10. A system according to claim 1 further comprising data processing modules on-board said platform, said data processing modules being for determining a spectral response of a plurality of pixels on said image gathering device to said light gathered from said specific target location based on a traversal angle for said interferometer.

11. A system according to claim 10 wherein said system determines said vertical column densities of atmospheric trace gases by recursively adjusting parameters of a predetermined model and recursively comparing said spectral response from said image gathering device with results from said model to determine said vertical column densities of said atmospheric trace gases at said specific target location, said vertical column densities being values which account for relevant atmospheric spectroscopy and a full instrument response from devices on said platform.

* * * * *